United States Patent [19]

Humphrey

[11] 4,199,816
[45] Apr. 22, 1980

[54] OPTICAL CALIBRATION APPARATUS AND PROCEDURE

[75] Inventor: William E. Humphrey, San Leandro, Calif.

[73] Assignee: Humphrey Instruments, Inc., San Leandro, Calif.

[21] Appl. No.: 920,313

[22] Filed: Jun. 28, 1978

[51] Int. Cl.$^2$ ............................................. G01B 11/00
[52] U.S. Cl. .................................. 364/571; 356/124; 356/127; 364/525
[58] Field of Search ............... 356/388, 394, 395, 398, 356/124–127, 399; 364/571, 525; 250/201

[56] References Cited

U.S. PATENT DOCUMENTS

| | | | |
|---|---|---|---|
| 3,671,748 | 6/1972 | Friedman | 250/201 |
| 3,762,821 | 10/1973 | Bruning et al. | 356/127 X |
| 3,836,258 | 9/1974 | Courten et al. | 356/399 X |
| 3,847,485 | 11/1974 | Zanoni | 356/125 X |
| 3,912,395 | 10/1975 | Voggenthaler | 356/125 X |
| 4,078,171 | 3/1978 | Stauffer | 250/201 |
| 4,082,463 | 4/1978 | Dehait et al. | 356/167 |
| 4,090,790 | 5/1978 | Dragon et al. | 356/125 |
| 4,102,575 | 7/1978 | Lapornik et al. | 356/125 |
| 4,123,163 | 10/1978 | Chace et al. | 356/127 X |
| 4,133,606 | 1/1979 | Hosoe et al. | 250/201 X |

Primary Examiner—Edward J. Wise
Attorney, Agent, or Firm—Townsend and Townsend

[57] ABSTRACT

A process and apparatus for the calibration of an optical instrument. An optical instrument—such as a lens meter or ophthalmometer—is provided with a light source, a light detector, and an optical train of assembled optical elements therebetween. A suspect optical element to be measured is placed within the optical train at a measuring interval to deflect light passing along the optical train. An occulting moving boundary locus having at least two boundaries of differing shape, and a dedicated computer may be used to measure beam deflection. The dedicated computer also makes use of stored computer constants to transform raw measurements into the desired optical properties of the suspect optical element. The optical train of the instrument has its assembled optical elements randomly placed to production tolerances; precision registration of the optical elements to traditional close optical tolerances is omitted. Calibration occurs by manipulating the instrument's beam deflection apparatus under the control of a calibration program, by providing the optical instrument being calibrated with an umbilical cord which bypasses the central processing unit of the dedicated computer, but otherwise manipulates the entire optical instrument's beam deflection apparatus. This umbilical cord leads from a calibration computer, which substitutes central processing and contained memory as well as providing a supplemental program for the generation of customized computer constants. Customized computer constants are generated for each instrument by insertion of a series of test elements of known quantity into the samping interval of that instrument, and burned into a memory which is then placed into the dedicated computer of the instrument being calibrated.

19 Claims, 8 Drawing Figures

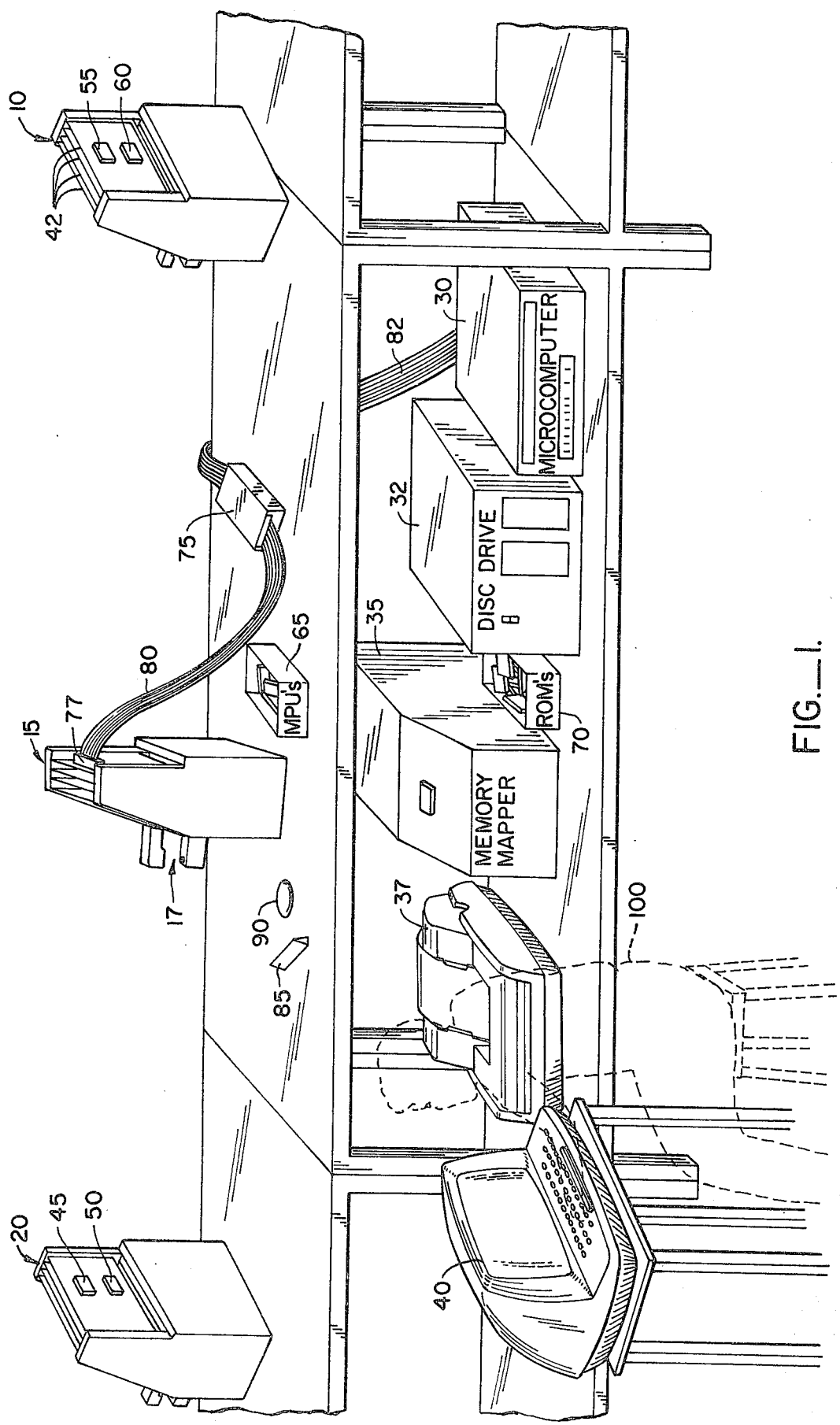
FIG._1.

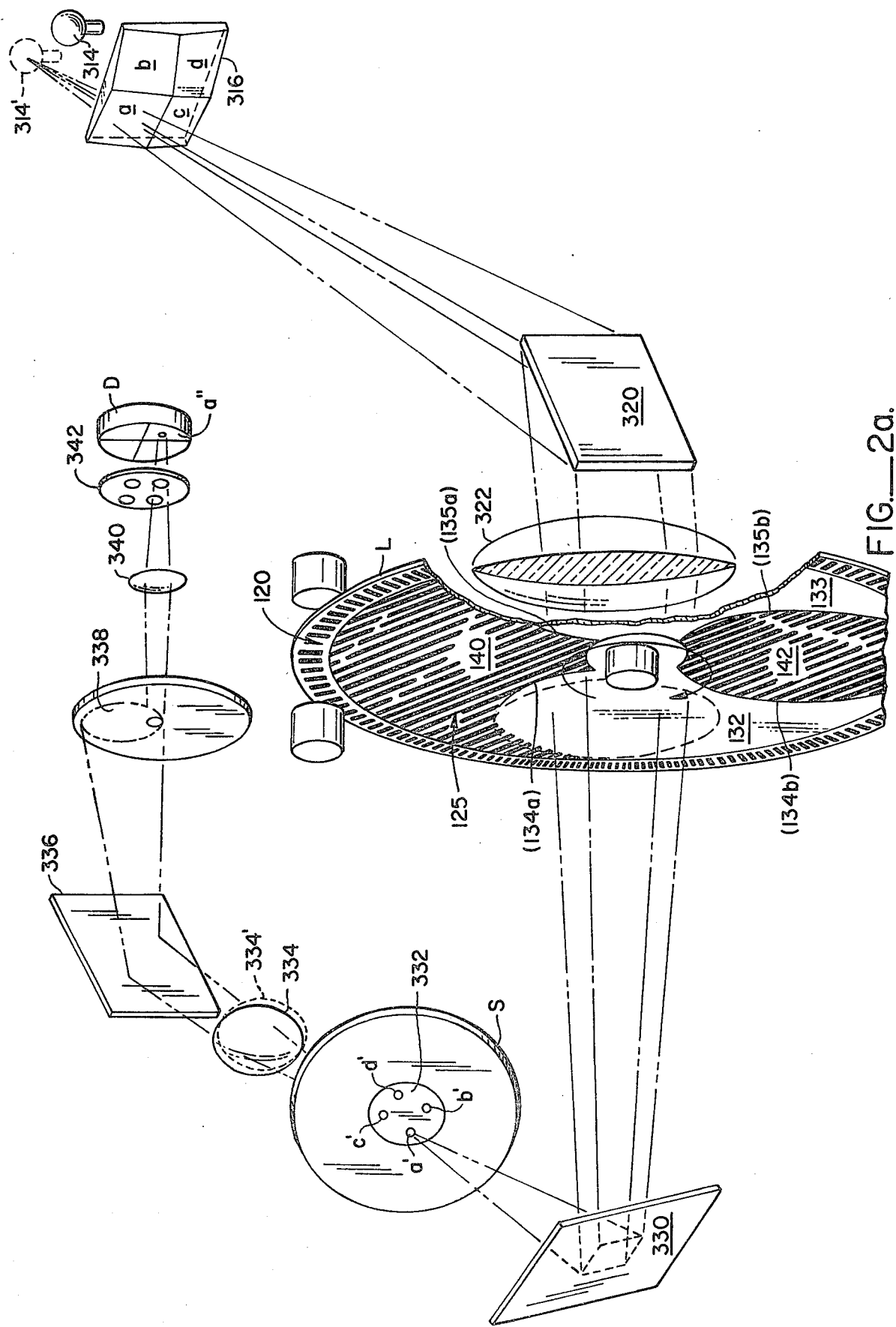
FIG._2a.

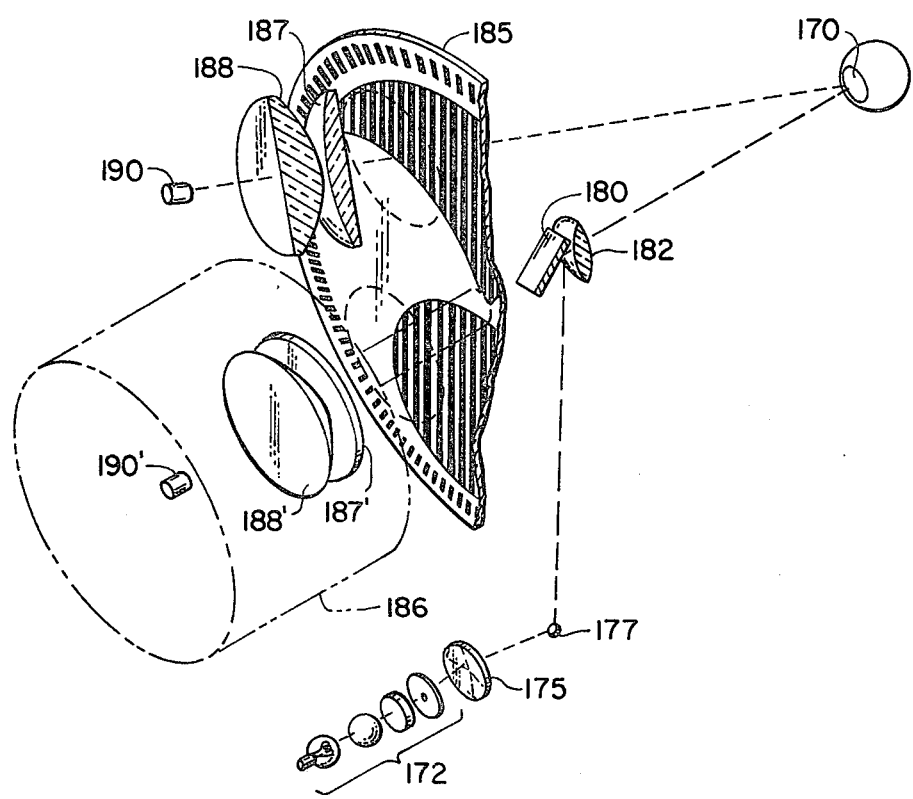
FIG._2b.

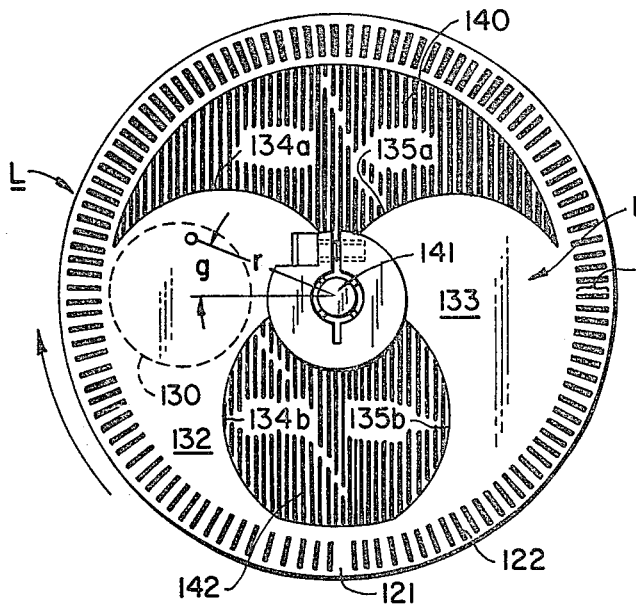
FIG._3.
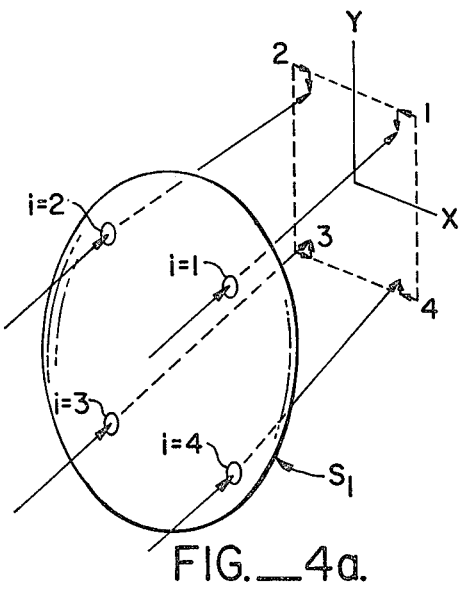
FIG._4a.
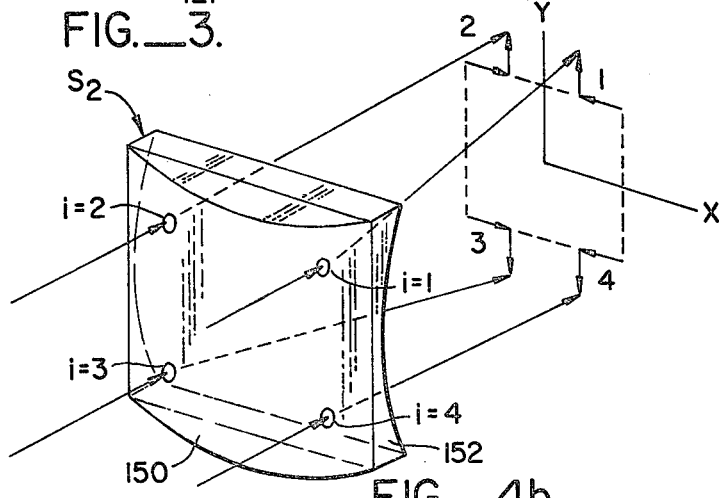
FIG._4b.
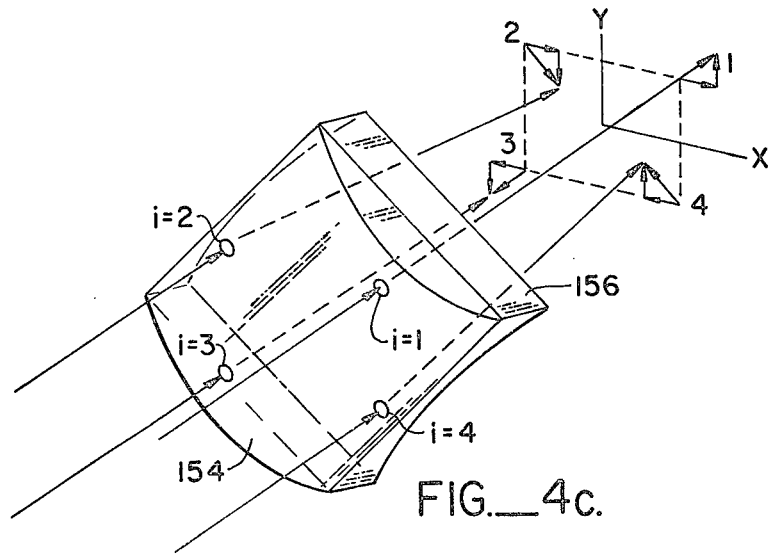
FIG._4c.

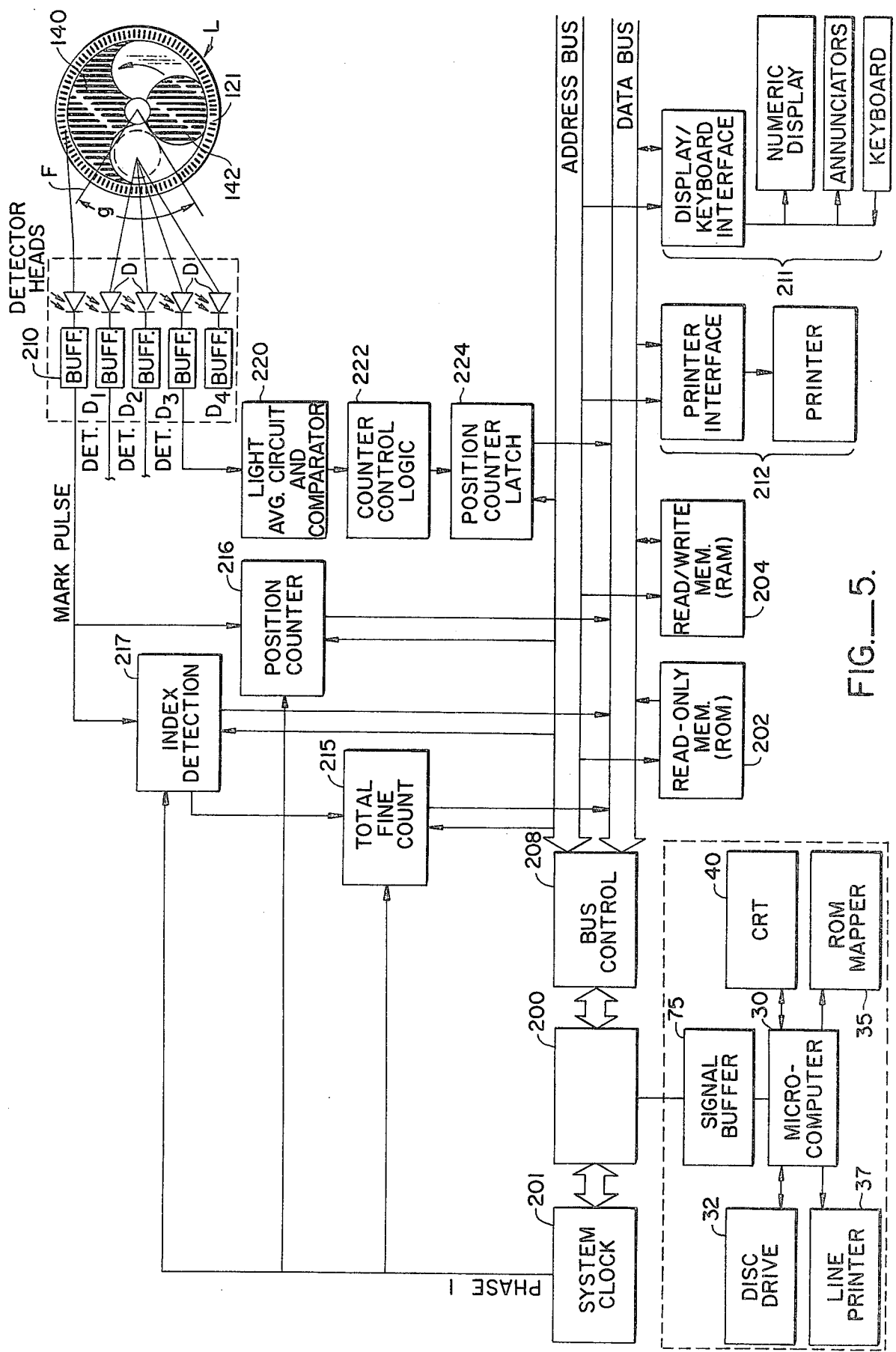
FIG._5.

OPTICAL CALIBRATION APPARATUS AND PROCEDURE

This invention relates to a calibration procedure for optical apparatus, such as an automated lens meter or automated ophthalmometer.

SUMMARY OF THE PRIOR ART

Heretofore, an optical instrument such as a lens meter or an ophthalmometer has had its individual optical elements aligned with precision at the time of production. Typically, great care is taken to register each of the optical elements, so that the overall instrument error is minimal. A great deal of time has been consumed in such optical element registration.

According to the present invention, an optical instrument having a dedicated computer has its optical train permanently assembled to relatively loose production line tolerances. Measurements by the instrument of optical elements having known properties are used to generate a set of customized optical constants that become associated with that instrument's dedicated computer before the instrument leaves the production facility.

The broad concept of instrument self-manipulation, that is using the instrument's output to calibrate the instrument itself, has not been used generally outside the bubble chamber and streamer chamber arts. In those particular arts, subatomic particle tracks in a chamber are photographed from at least two spatially separated views. Included in each photograph, millions of which may be taken in a typical experiment, are the images of certain bench marks or "fiducials" which are located at various places within or about the chamber.

The photographs are subsequently digitized for the purpose of reconstructing the particle tracks in space. In this step of the analysis, at least some of the fiducial images are used to register the photograph in the image plane. However, the spatial reconstruction cannot proceed without a knowledge of the optical parameters of the system, such as fiducial locations in space, camera locations, focal lengths, lens distortion parameters, and lens and film plane axis tilts. Thus a procedure known as optical fitting in which a set of "optical constants" is generated must be carried out.

For the purpose of optical fitting, an extended set of fiducials (beyond the minimum number needed to register the film) is photographed and the photographs digitized to provide image plane locations of the fiducials. A set of optical constants that gives the best agreement between the measured fiducial positions on film and the predicted fiducial positions on film (based on the optical constants) is determined by a $\chi^2$ (chi squared) minimization technique. These constants are then used in the spatial reconstruction. It is not necessary to generate new optical constants for each photograph since the optical constants do not change unless the apparatus itself changes. Several sets of constants may be generated to check apparatus consistency over time.

With respect to the lens meter and ophthalmometer art, these optical fitting techniques have only limited applicability. In particular, the provision of a fixed set of fiducials would have little meaning in an instrument which measures beam excursion in the region between a fixed source and a fixed detector. In effect, it would be necessary to provide the instrument with many more light sources and optical paths for calibration than were actually necessary for measurement. Moreover, the additional light paths would represent measurements of something qualitatively different from that which the instrument was meant to measure. This is only partly true in the bubble chamber and streamer chamber situations since the fiducials give rise to light paths that are typical of those that arise for some particle track configurations. Nevertheless, it can be seen that the bubble chamber and streamer calibration techniques only involve instrument self-manipulation in an approximate sense. Since they are devices for measuring particle tracks, a truly self-manipulative calibration procedure would involve the determination of optical constants from actual particle track measurements where the particle momentum or other parameters are known. In any event, the application of an interrogating computer to in effect align individual optical elements on a permanent basis at the end of a production line is nowhere disclosed or suggested to applicant's knowledge in this prior art.

Finally, it is known to manipulate electronic computers at their central processing units during an assembly stage. In such devices, an outside computer is wired or connected to the central processing unit of a unit being produced and in effect substituted for that central processing unit. Once this is done, the program of the computer is tested; for example, it may be single stepped, trapped, or have its various memory conditions checked. However, such central processing unit substitutions in the prior art have not been used for the purpose of optical alignment of an entire optical instrument through self-manipulation.

SUMMARY OF THE INVENTION

The present invention provides for precision calibration of an optical instrument without the necessity of precision alignment. An optical instrument—such as a lens meter or ophthalmometer—is provided with a light source, a light detector and an optical train of assembled optical elements for passing light from the light source to the detector. A suspect optical element to be measured is placed within the optical train at a measuring interval to deflect light passing along the optical train—this deflection being reflection by a suspect lens in the case of a lens meter, and reflection by a suspect cornea in the case of an ophthalmometer. An occulting moving boundary locus having at least two boundaries of differing shape, and a dedicated computer may be used to measure beam deflection. The dedicated computer also makes use of stored computer constants to transform raw measurements into the desired optical properties of the suspect optical element. These desired values may be printed out on a dedicated printer.

The optical train of the instrument has its assembled optical elements randomly placed to production tolerances; precision registration of the optical elements to traditional close optical tolerances is omitted. Calibration occurs by manipulating the instrument's beam deflection measurement apparatus under the control of a calibration program. The calibration program may be stored in a separate calibration computer, and calibration carried out by providing an umbilical cord between the optical instrument being calibrated and the fixed calibration computer. This connection bypasses the central processing unit (hereinafter CPU) of the dedicated computer, but otherwise manipulates the entire optical instrument's beam deflection apparatus. The calibration computer substitutes central processing and contained memory as well as providing the supplemental program for the generation of customized computer constants.

Customized computer constants are generated for each instrument by insertion of a series of test elements of known quantity into the samping interval of that instrument. That is, measurements are made wherein the optical properties of the suspect elements are known, but the various scale factors, points of origin, angular corrections, and the like, of the instrument are not known, but rather are to be determined. These constants, upon generation, are burned into a memory which is then placed into the dedicated computer of the instrument being calibrated. The umbilical system is then disconnected, the instrument's computer is activated, and the instrument leaves the assembly line.

Alternately, the calibration program may be run under the control of the dedicated computer's CPU with the calibration program stored in an auxiliary memory. The customized constants may then be printed on the instrument's printer and manually entered into a memory for subsequent placement into the dedicated computer.

By this process, optical elements randomly placed in the optical train to production tolerances, are utilized without individual registration to exact calibrated position. Apparatus calibration on a rapid and automated basis results.

SUMMARY OF THE CALIBRATION COMPUTATIONS

First, occultation information is taken where no suspect element is in the sampling interval (i.e. null element information). Thus, no deflection is expected to occur.

Second, a prism is placed in the sampling interval and occultation information recorded. The prism is then rotated through one or more known angles, e.g., 90° or 180°, and further occultation information generated. On the basis of the prism and null element occultation information, the points of origin and scale factors that allow a transformation of raw occultation information to beam deflections are computed. Moreover, the relative angle between the coordinate system of the lens table and that defined by the sampling apertures can be computed.

Third, occultation information is taken with one or more test elements having known spherical and/or cylindrical power. This is used to correct the constants computed above.

The knowledge that circular astigmatism of the sphere test element must be zero is exploited. In particular, the parameters that have been computed in the above steps do not guarantee that circular astigmatism is zero for those measurements. However, it is possible by rotating the coordinate system to insure that the circular astigmatism vanishes. The rotation effectively corrects for any misalignment of the sampling apertures. This rotational correction is applied to the scale factors and points of origin that had been computed on the basis of the prism and null element occultation information.

Fourth, the spherical scale factor is computed. With the corrected constants, deflection information for the null element and sphere test element occultation information is computed. The corrected sphere deflections relative to the corrected null element deflection information give rise to a spherical equivalent which can then be divided into the known spherical power to provide the scale factor.

Fifth, the points of origin for sphere and cross cylinder are computed on the basis of the corrected deflections from the null element occultation information.

OTHER OBJECTS AND ADVANTAGES

An object of this invention is to provide for complete assembly of an optical instrument without requiring precision alignment of the individual optical elements of the instrument. According to this aspect of the invention the optical train of an optical instrument between a light source and light detector has its individual optical elements randomly placed to production tolerances only. Precision registration of the optical elements is omitted. Light deflection measuring apparatus, such as an occulting moving boundary locus and a dedicated computer, is used to measure beam deflection. The instrument is provided with an umbilical connection which allows communication with a calibration computer. The calibration computer when connected completely supplants the function of the instrument's own central processing unit. By insertion of a series of test elements of known quantity into the sampling interval, customized computer constants are generated for each instrument having its randomly aligned optical train. By the expedient of placing the generated constants into the dedicated computer of the individual optical apparatus, calibration on a rapid and automated basis results.

An advantage of this invention is that laborious assembly line procedures of individual optical element calibration are avoided. Optical elements are merely placed in the instruments firmly within production tolerances. As those assembling the machine have a relatively wide latitude for the placement of optical elements, production is greatly expedited.

A further advantage of this invention is that the disclosed calibration technique requires each instrument to verify its own function. Through the intercession of an outside computer which manipulates the instrument, each of the active elements of the produced optical apparatus can be manipulated and verified. The required instrument constants are generated through manipulation of the very instrument in which they are required. Consequently, the instrument constants are generated to a high degree of accuracy.

Yet another advantage of this invention is that it is possible to obtain an automated record of instrument production. Since, in the production of medical instruments, it is customary for the manufacturer to maintain individually tailored records for each produced instrument, the disclosed calibration procedure readily meets this requirement. A record parochial to each instrument is generated, which record not only records instrument identification data, but additionally all customized computer constants.

A further advantage of this invention is that the calibration computer is utilized to pass or reject instruments. Where, for example, an instrument is far out of alignment, provision can be made to automatically reject such an instrument. Moreover, a manipulating calibration computer can identify problem areas which can then be corrected.

A further object of this invention is to disclose an optical instrument produced with an umbilical connection which can, throughout the life of the instrument, provide for exterior manipulation and calibration of the instrument by a calibrating computer. According to this aspect of the invention, the optical apparatus includes an umbilical connection, which upon connection to a calibrating computer supplants the function of the instrument computer with an outside computer, so that instrument manipulation and monitoring can occur.

An advantage to this aspect of the invention is that the produced instrument with its attached umbilical connection can at any time during its useful life be manipulated. By manipulation, those components requiring repair can be identified and replaced. Thereafter, rapid and automated calibration of the instrument, as well as the generation of recorded test data, can occur. True quality control results.

A further object of this invention is to adapt a precision calibration technique to a production line assembly of a precision optical instrument. According to this aspect of the invention, lens meters on the production line are sequentially examined at a quality control station by a manipulating calibration computer. The instruments are examined in wide tolerances for a pass-fail standard; subsequently, the instruments are precision calibrated by customized computer constants and tested in a wide variety of measurement functions. Thereafter, the customized computer constants are placed in the machine and the instrument is ready for use.

An advantage of this aspect of the invention is that the calibration procedure can remotely indicate to the calibration operator those procedures to follow, as well as whether the instrument has passed or failed such procedures. Not only can the calibrating operator be relatively unskilled in the optical alignment arts, but additionally, little room is left for operator error.

A further object of this invention is to provide an improved calibration procedure for determining scale factors and points of origin for the geometrical and optical properties of an optical instrument. According to this aspect of the invention raw data (e.g. occultation information) is generated for: no test element; prism test element (at least two orientations having known angular separation therebetween); and one or more sphere and/or cylinder test elements.

An advantage of this aspect of the invention is that the null element and prism information alone can be used to generate the geometric scale factors and points of origin which allow raw occultation information to be converted to deflection information. The fact that the sphere test element does not exhibit non-toricity (in particular circular astigmatism) can then be used to compute a coordinate system rotation which corrects for misalignment of the sampling apertures.

Another advantage of this aspect of the invention is that the spherical element information can then be combined with the null element information to generate the optical scale factor and points of origin that allow deflection information to be converted to the desired form of optical parameters (sphere, cylinder, axis, etc.). The fact that the geometric points of origin and scale factors had been corrected for spurious non-toricity effects allows the use of zero-going test functions (e.g. functions such as circular astigmatism whose non-zero values indicate the presence of non-toric surfaces) to serve as diagnostics in the computations carried out by the calibrated instrument in actual use.

Other objects, features and advantages of this invention will become more apparent after referring to the following specification and attached drawings.

BRIEF DESCRIPTION OF THE DRAWINGS

FIG. 1 illustrates an assembly line of optical instruments, here lens meters, being interrogated by a calibration computer at a quality control station on an assembly line.

FIG. 2a is a perspective schematic of optics inside one type of instrument—here a lens meter—capable of being calibrated by the method and apparatus of the present invention.

FIG. 2b is a perspective schematic of optics inside another type of instrument—here an ophthalmometer—capable of being calibrated according to the present invention.

FIG. 3 is a plan view of a moving boundary locus disc suitable for measuring beam deflections in a lens meter or keratometer.

FIG. 4a is a perspective schematic illustrating beam deflections caused by a suspect element having spherical power.

FIG. 4b is a perspective schematic illustrating beam deflections caused by a suspect element having 0°–90° astigmatism.

FIG. 4c is a perspective schematic illustrating beam deflections caused by a suspect element having 45°–135° astigmatism.

FIG. 5 is a block diagram of computer logic illustrating with particularity the point of supplementation of the dedicated computer logic by the attached umbilical cord to provide for manipulation of the entire instrument and individual instrument participation in the generation of its own constants.

DESCRIPTION OF THE PREFERRED EMBODIMENT

Overview of the Calibration Procedure

FIG. 1 is a somewhat stylized view of an assembly line calibration station. In this picture, lens meters are being calibrated—lens meter 10 is awaiting calibration, lens meter 15 is being calibrated, and lens meter 20 has just been calibrated at this calibration station. An important feature of this invention is that these lens meters have had their optical components assembled to relatively loose production tolerances, and that no further precision alignment is required.

The apparatus at the calibration station is, broadly, an interrogating and calibrating computer system, the components of which include microcomputer 30, associated disc drive 32, memory mapper 35, printer 37, and display console 40. Lens meter 10 awaiting calibration, has associated electronics, the components of which are mounted on boards 42. As will be described in detail below, the associated electronics includes a dedicated computer having a microprocessor unit (hereinafter MPU) and a read-only memory (hereinafter ROM). Lens meter 20, shown leaving the calibration station, has MPU 45 and ROM 50 in place, shown for simplicity as being mounted on the same board. In advance of calibration however, lens meter 10 has MPU socket 55 and ROM socket 60, neither of which has its associated component in place yet. In principle, it is possible for lens meter 10 to have its MPU and ROM installed, but since the calibration procedure requires that the ROM be inserted into memory mapper 35 and that the MPU be removed, it is more feasible to have a supply of MPU's 65 and a supply of ROM's 70 at the calibration station. During the calibration step, microcomputer 30, is connected to the MPU socket of lens meter 15 (undergoing calibration) through signal buffer 75 and plug 77. Signal buffer 75 and plug 77 are connected by multiconnector cable 80; microcomputer 30 and signal generator 75 are connected by multiconnector cable 82. The effect of this connection between microcomputer 30 and lens meter 15 is that the calibration computer is substituted for the dedicated computer.

During the calibration step, a series of test elements which may include a prism 85 and a lens 90 are sequentially inserted into the sampling interval 17 of lens meter 15. The insertion and replacement of test elements, as well as the inputting of instructions to the calibration computer, are done by calibration operator 100 shown in phantom outline seated at the console 40.

OPERATION OF THE CALIBRATED INSTRUMENT

While FIG. 1 is drawn most specifically to lens meter calibration, the method and apparatus of this invention wherein a fixed calibration computer is substituted for each instrument's dedicated computer, is suitable for calibrating any optical instrument which makes use of a dedicated computer to manipulate internal constants in order to provide intelligible measurements to the user. The mathematical analysis that will be discussed below is concerned with the transformation of raw data in the form of beam measurements in order to obtain desired optical parameters in terms of sphere, cylinder, cylinder axis, and prism. This is merely illustrative, the technique being applicable to a broader class of instruments. The discussion below will also be most specifically descriptive of an instrument wherein the beam deflection is measured by a moving boundary locus. Both a lens meter for analyzing refractive suspect optics and an ophthalmometer for analyzing reflective suspect optics will be discussed.

In order that the details of the mathematical analysis of the calibration procedure be understood and appreciated, a digression is made to explain the operation of particular embodiments of lens meters and ophthalmometers. Both the apparatus for the generation of raw measurements of beam deflection, and the mathematics for transforming these raw measurements into optical parameters are now considered.

FIG. 2a shows a lens meter in which a moving boundary locus is utilized to measure the deflection, caused by suspect optical element S, of a beam between light source 314 and detector D. This configuration makes use of a beam wherein the light rays are not parallel to one another.

Briefly, a single light source 314 is imaged in multifaced prism 316 to produce four apparent light sources, one of which is designated as 314'. FIG. 2a illustrates the optical path from apparent light source 314', it being understood that three additional optical paths, omitted for clarity, are also present. The light from virtual image 314' is divergent. The light is reflected from diagonal mirror 320 and then focused by condensing lens 322 which renders the light convergent. From lens 322, the light is reflected from mirror 330 and passes through aperture plate 332. Aperture plate 332 preferably has a separate aperture for each apparent light source. The suspect optical element S is typically registered to aperture plate 332 and each apparent light source is imaged as a tiny intense spot of light at its corresponding aperture. Thus, each aperture serves to sample a distinct region of the suspect optical element.

After passing through one of the apertures, here aperture a', the light passes through a lens 334, is reflected from mirror 336, and falls on sampling mask 338. Sampling mask 338 has a central aperture which limits the amount of light to an angularly smaller bundle. The light then passes through lens 340 and mask 342, to a sector a' of detector D corresponding to virtual light source 314' and sampling aperture a'.

Depending on the optical power of suspect element S, the actual optical path of the light between light source 314 and detector D will be subject to deflection. Moving boundary locus L which is, in the embodiment shown, a rotating disc is situated between lens 322 and mirror 330, but typically closer to lens 322. As is more clearly shown in FIG. 3, moving boundary locus L has a border area 120 which defines disc rotation, and internal region 125 which occults the deflected light beams. Internal region 125 comprises opaque areas 140 and 142, and transparent areas 132 and 133. Each of the four light paths corresponding to the four facets of prism 316 falls on a different region of the rotating disc and may be treated as completely independent of the other three. The boundaries between opaque areas 140 and 142, and transparent areas 132 and 133 can be described generally by the equations $$R = k\theta \text{ and } R = -k\theta$$

where R and $\theta$ are the radial and angular coordinates, and k is a proportionality constant. As the disc rotates, the light impinging on the disc is alternately transmitted and occulted. A knowledge of the angular position of the disc when occultation occurs also permits knowledge of the radial position on the disc. The known relation between angle and radius defines the boundaries between the opaque and the transparent areas. Once radial and angular position are known, beam deflection is defined.

The details of the optical train and moving boundary locus of FIG. 2a are more fully set forth in my copending U.S. Patent Application Ser. No. 813,211, filed July 5, 1977, entitled "Lens Meter with Automated Read-Out". I hereby incorporate by reference my earlier above-identified U.S. Patent Application. This application is abstracted as follows:

"An automated readout for a lens meter is disclosed in combination with a light beam deflecting type of lens meter such as that of a Hartman test. In such a light beam deflecting type of lens meter, a light source having one or more beams is passed through a suspect optical system and deflected by the suspect optical system to a deviated path. Measurement of the deviated path within a preselected area of excursion is typically equated to various powers of the suspect optical system in sphere, cylinder, cylinder axis, and prism. The invention provides for a means of measurement of deviate paths and includes a moving boundary locus with edges of distinctly different shape placed to intercept and occult said deflected beam in a known plane within the area of excursion at a distance from the suspect optical system. The moving boundary locus is typically arranged for movement along a predetermined path at a velocity within the known plane. The boundary locus includes a first substantially transparent portion, a second, substantially opaque portion, and at least two boundaries between the opaque and transparent portions. Each of the two boundaries defines a unique nonambiguous intersection within the area of excursion for each position of the beam and sweeps the preselected area of excursion at differing angularities with respect to the predetermined path of said moving boundary locus. The beam, after leaving the moving boundary locus, is reimaged to a photosensitive detector. By the expedient of measuring the position of the moving boundary locus when the moving boundary occults the beam for two of the boundaries, the amount of beam excursion can be measured and related to optical system measurement. The detector is provided with a circuit which averages the two detector states provided by occultation. This enables lens systems of varying light transmissivity to be measured."

A representative patent claim is a follows:

"1. In the combination of a suspect optical system for measurement of deflection, a light source emanating a beam passed through said suspect optical system and deflected by said suspect optical system to a deviated beam path for measurement within a preselected area of excursion; and, means for measurement of said deviated path, the improvement in said means for measurement of said deviated path comprising: a moving boundary locus placed in a known plane at a preselected distance from said suspect optical system; said moving boundary locus arranged for sweeping movement along a predetermined path within said known plane, said boundary locus including a first portion, a second portion and at least two boundaries therebetween of distinctly different shape with each of said boundaries sweeping at differing angularities with respect to the predetermined path of said moving boundary locus; means for sweeping said moving boundary locus along said predetermined path producing occulation of said beam by said boundaries; a photosensitive detector aligned to receive said beam; and, means for measuring the position of said moving boundary locus when said detector detects produced occultation of said light beam at said boundaries of said moving boundary locus whereby at least one measurement of each of said moving boundaries of said moving boundary locus at the time of detector detection of occultation measures the excursion of said beam due to deflection by said suspect optics."

FIG. 2a is copied from the above-referenced application, being designated there as FIG. 8. The only changes that have been incorporated into FIG. 2a are the addition of reference numerals for the moving boundary locus portions, and the addition of dashed outline 334'.

FIG. 2b shows the optical train of an ophthalmometer used to measure reflective power, here that of a cornea 170. A single light source 172 is imaged in a multifaced prism 175 to produce four virtual images and thus establish four separate light paths between light source 172 and cornea 170. For clarity, only one of the light paths from light source 172 to cornea 170 is shown. The light from each virtual image of light source 172 is divergent. It is reflected from a small elliptical diagonal mirror 177 which serves both as a reflector and an aperture stop. Light reflected by mirror 177 then passes to a mirror 180, and through a focusing lens 182 to the suspect cornea.

Each of the four virtual images of light source 172 is thus focused on a separate portion of cornea 170. The light reflected from cornea 170 is then intercepted by a moving boundary locus disc 185, the precise position of interception depending on the curvature of cornea 170 which is being measured. The operation of disc 185 is substantially the same as for the lens meter described above. Moving boundary locus disc 185 is driven by a motor 186, shown in phantom. The light is then focused by light collecting optics defined by lenses 187 and 188 before passing into a detector 190.

Due to the geometry of the ophthalmometer, the light from the four virtual images, once reflected off cornea 170, follows four widely separated light paths and falls on four discrete portions of locus disc 185. Four separate light collecting optical subtrains and four detectors are used. Also shown in FIG. 2b are a detector 190' and light collecting lenses 187' and 188' for a second of the four light paths. For clarity, the other two detectors with associated light collecting optics are not shown.

A comparison of the ophthalmometer with the lens meter shows the two devices to operate in essentially the same manner. Differences in geometry result from the need to accommodate reflective optics generally and horizontal axis reflective optics (e.g., a patient's eye) specifically. It should be noted that the lensmeter of FIG. 2a has a single optical train between the four light sources and the four detectors. The ophthalmometer of FIG. 2b, on the other hand, has four separate light collecting optical subtrains for the four detectors which are widely separated in space. Thus the ophthalmometer geometry is characterized by more internal constants for transforming raw occulation information into beam deflections.

Thus, the apparatus illustrated in FIGS. 2a and 2b produces, for a given suspect optical element, a total of 16 readings. That is, for each of the four sampling apertures, there are four angles of occulation corresponding to the four boundaries on the rotating disc, each boundary of which sweeps all four light beams. These hardware-generated values are designated as $\phi_{ij}$, where i designates the particular aperture (i.e., the particular light path or sampling interval on the suspect optical element), and j designates the particular boundary effecting the occulation. The numbering of the subscripts i and j is best understood with reference to FIG. 3 and FIGS. 4a–c. With reference to the disc shown in FIG. 3, border 135b corresponds to j=1; border 135a to j=2; border 134a to j=3; and border 134b to j=4. Reference to FIGS. 4a–4c shows that the positive x, positive y quadrant corresponds to i=1; the negative x, positive y quadrant to i=2; the negative x, negative y quadrant to i=3; and the positive x, negative y quadrant to i=4.

Computation of optical parameters of a suspect optical element from the raw occulation measurements $\phi_{ij}$, while comprising a long series of steps, can be better understood in terms of a smaller number of broader steps.

First, raw occulation information must be transformed into beam deflections measured in a transverse plane. In particular, scale factors and points of origin are applied to the raw occulation measurement to compute deflections. For the rotating boundary locus, these deflections are initially computed in polar coordinates so as to give radial and azimuthal deflections. These may then be transformed to cartesian coordinates.

Second, the deflections of the beams are manipulated to provide a plurality of numbers having certain physical significance. In particular, with four sampling apertures and a deflection in two dimensions for each, eight pieces of deflection information are produced. These are more conveniently rearranged to provide a new set of independent pieces of information. In the preferred embodiment, two prism measurements, two cross cylinder astigmatism measurements, and a spherical equivalent measurement are computed. This leaves three more pieces of information available. It is convenient and useful to compute three optical quantities that are expected to be zero for most optical elements. Thus, circular astigmatism and two power variation parameters are computed.

Third, a scale factor representing spherical power is applied to six of the eight optical quantities that had been computed in terms of deflections. The prism measurements are not scaled.

Fourth, suspicious circumstances are flagged using the extra (but not redundant) information. For example, the values of circular astigmatism and power variation are compared with predetermined numerical values as a check that the optical element being measured does not possess these unexpected properties. In particular, if either circular astigmatism or the quadratic sum of the power variation parameters is larger than a predetermined value, a suspicious circumstance is flagged.

Fifth, desired forms of optical parameters are calculated. The two values representing cross cylinder astigmatism are converted into cylinder and cylinder axis. In order to accomplish this, it is necessary to remain aware of the fact that the coordinate system in which the deflections were measured is not in general oriented with respect to the coordinate system of the lens table with which the suspect optical element is aligned. Thus, an angular correction to the cylinder axis and prism measurement must be made. In addition, points of origin for sphere and cylinder measurement must be taken out and spherical equivalent must be corrected for cylinder to produce the desired value of sphere. This step may be carried out before the fourth if desired.

Having thus described in general the computations carried out by the calibrated instrument in actual use, a more detailed mathematical description can be set forth. This description must be made with reference to a particular instrument geometry. The lens meter computations are now set forth. The ophthalmometer computations are analogous, but would involve separate constants for transforming raw occulation information into beam deflections.

First, the occultation data in terms of $\phi_{ij}$ must be converted to beam deflections $x_i$ and $y_i$.

For a given aperture i, the quantity $f_i$ can be written where:

$$f_i = \phi_{i3} + \phi_{i4} - \phi_{i1} - \phi_{i2} \quad (1)$$

It can be seen that the quantity $f_i$ is a measure of the radial position at which the $i^{th}$ beam crosses the plane of the rotating disc. A measure of the azimuthal position of the beam is given by the quantity $g_i$ where:

$$q_i = \phi_{i1} + \phi_{i2} + \phi_{i3} + \phi_{i4} \quad (2)$$

Since the angular separation between boundaries 135a and 135b is a constant 90° regardless of radius, and similarly the angular separation between borders 134a and 134b is 90°, the quantity $t_i$ where:

$$t_i = \phi_{i1} + \phi_{i4} - \phi_{i2} - \phi_{i3} \quad (3)$$

provides a check on the system since $t_i$ should be nearly zero.

The radial deflection $R_i$ and angular deflection $\phi_i$ for the beam from the aperture i can be written in terms of $f_i$ and $g_i$ as follows:

$$R_i = \alpha f_i + \beta \quad (4a)$$

$$\phi_i = \gamma g_i + \delta \quad (4b)$$

The parameters $\alpha$, $\beta$, $\gamma$, and $\delta$ are constants for a given instrument, these constants, among others, being generated in the calibration procedure that is the subject of this application. (The calibration procedure is described below.) In particular, $\alpha$ is related to the equations of the contour ($R = k\theta$ and $R = -k\theta$); $\beta$ takes up the radial position with no radial deflection to provide $R_i = 0$; $\gamma$ is a constant of proportionality that is known independently of the calibration of the instruments, being a function of the number of divisions in the outer portion of the rotating disc; and $1\delta$ determines the zero of angle.

The radial deflection $R_i$ and the angular deflection $\phi_i$ for each sampling aperture are then transformed to deflections in cartesian coordinates by the standard formulae:

$$x_i = R_i \cos \phi_i - x_0 \quad (5a)$$

$$y_i = R_i \sin \phi_i - y_0 \quad (5b)$$

where $x_0$ and $y_0$ are parameters corresponding to the cartesian coordinates of the undeflected light beams.

Having obtained the vertical and horizontal cartesian deflections for each sampling aperture, it is possible to calculate combinations of the deflections that are more closely related to optical parameters. Thus, horizontal prism $P_x$ and vertical prism $P_y$ are given by the formulae:

$$P_x = \sum_{i=1}^{4} x_i \quad (6a)$$

$$P_y = \sum_{i=1}^{4} y_i \quad (6b)$$

$P_x$ and $P_y$ may be computed directly in terms of prism diopters if $\alpha$, $\beta$, $x_0$, and $y_0$ have been scaled with that in mind. In any event, $P_x$ and $P_y$ would only have to be scaled by a multiplicative factor to get the result in prism diopters.

FIGS. 4a-c show the beam deflections caused by suspect elements having sphere, 0°–90° astigmatism and 45°–135° astigmatism consists of a positive cylinder 154 aligned along the 45° axis and a negative cylinder 156 aligned along the 135° axis. It should be understood that such crossed cylinders as shown in FIGS. 4b and 4c are typically composite and do not have an optical interface between the positive and negative cylinders.

In terms of the cartesian deflections of the beams, it is possible to express spherical equivalent (Seq), 0°–90° astigmatism ($C_+$) and 45°–135° astigmatism ($C_x$) as follows:

$$\text{Seq} = -x_1 + x_2 + x_3 - x_4 - y_1 - y_2 + y_3 + y_4 \quad (7a)$$

$$C_+ = 2(+x_1 - x_2 - x_3 + x_4 - y_1 - y_2 + y_3 + y_4) \quad (7b)$$

$$C_x = 2(+x_1 + x_2 - x_3 - x_4 + y_1 - y_2 - y_3 + y_4) \quad (7c)$$

Seq., $C_+$, and $C_x$ may then be scaled by a multiplicative scale factor S so they are expressed in diopters.

The measurement of $P_x$, $P_y$, Seq, $C_+$, and $C_x$ is overdetermined in the sense that eight deflection quantities $x_i$ and $y_i$ measured and only five parameters are required. While the five parameters suffice to describe normal optical elements expected to be encountered, there are certain non-toric surfaces and surfaces having a power variation, possibly due to inhomogeneity of material, that can give rise to non-zero values of circular astigmatism (CA) and of power variation parameters ($PV_1$ and $PV_2$) where:

$$CA = +x_1+x_2-x_3-x_4-y_1+y_2+y_3-y_4 \quad (8a)$$

$$PV_1 = -x_1+x_2-x_3+x_4-y_1+y_2-y_3+y_4 \quad (8b)$$

$$PV_2 = +x_1-x_2+x_3-x_4-y_1+y_2-y_3+y_4 \quad (8c)$$

One possible method of transforming the beam deflections into sphere, cylinder, and prism as described above would be to adjust the x and y values through a $X^2$ minimization with the constraints that CA, $PV_1$ and $PV_2$ be zero. However, in the preferred embodiment, sphere, cylinder and prism are computed directly from the measured deflections, and CA, $PV_1$ and $PV_2$ also computed. Then, if CA or the PV's exceed a predetermined limit, this is taken to indicate a suspicious circumstance.

In particular, the following circumstances are flagged:

$$(S)(CA)>0.2 \text{ or} \quad (9a)$$

$$(S)\sqrt{(PV_1)^2+(PV_2)^2}>0.3 \quad (9b)$$

where S is the scale factor that transforms Seq, $C_+$, and $C_x$ to diopters. The limits of 0.2 and 0.3 are representative.

In fact, it is customary to describe lenses not in terms of Seq, $C_+$ and $C_x$, but rather in terms of sphere $S_1$, cylinder C, and azimuthal angle $\theta$. These two alternate sets of descriptive parameters are related by the following equations:

$$(S)(C_+) = C\cos 2(\theta+A)+Z_{c+} \quad (10a)$$

$$(S)(C_x) = C\sin 2(\theta+A)+Z_{cx} \quad (10b)$$

$$(S)(Seq) = S_1+C/2+Z_s \quad (10c)$$

Where, in addition to S, the quantities $Z_s$, $Z_{c+}$ and $Z_{cz}$ are parameters that have been determined during the calibration step to be described below. The parameter A is basically the relative angle between the x-y coordinate system of the apertures and the orientation of the lens table of the lens meter nessitating correction of $P_x$ and $P_y$. A parameter $d_1$ represents a small displacement of the lens measuring position along the optical train, necessitating correction of S, and C.

Thus, corrected prism values $P_x'$ and $P_y'$, sphere $S_1'$, and cylinder $C'$ are given by:

$$P_x' = P_x\cos A + P_y\sin A \quad (11a)$$

$$P_y' = P_y\cos A - P_x\sin A \quad (11b)$$

$$S_1' = S_1/[1+(d_1)(S_1)] \quad (11c)$$

$$C'+S_1' = (C+S_1)/[1+(d_1)(C+S_1)] \quad (11d)$$

At this point, it can be seen that the computation of sphere, cylinder, cylinder axis, and prism can be accomplished from the raw input of the $\theta_{ij}$, so long as the instrument has been calibrated to provide values of $\alpha$, $\beta$, $\gamma$, $\delta$, $X_0$, $Y_0$, $S$, $Z_s$, $Z_{C+}$, $Z_{CX}$, A, and $d_1$.

The electronic circuitry required to ultimately calculate the desired quantities of sphere, cylinder, axis, and prism performs four logical functions. First, the rotational position of the rotating boundary locus L is monitored. Second, the occulations are recorded as they occur. Third, the circuitry computes the angular interval of the occulation in terms of the $\theta_{ij}$, typically to an accuracy of 1 part in 50,000 of the total rotation. Fourth, these angular values are converted to the desired parameters using the formulae discussed above.

FIG. 5 is a schematic block diagram of the electronic circuitry to perform these various functions and also the circuitry that accomplishes the calibration. The operation of the lens meter (or other instrument) circuitry is more fully described in my copending U.S. Pat. Application Ser. No. 813,211, filed July 5, 1977, and incorporated by reference above. FIG. 5 of the present application is substantially identical to FIG. 4 of the referenced application, except that blank block 200 was formerly shown to contain a CPU and the circuit elements within dashed rectangle 230 have been added. The circuit elements within dashed rectangle 230 are only connected with the rest of the circuit during the calibration step, and when the calibration is over, those elements are disconnected and a CPU chip (preferably a type 8080 MPU manufactured by Intel Corporation of Santa Clara, California) is inserted in the socket corresponding to blank rectangle 200. When the instrument with its own CPU is doing the computations required for a measurement of the suspect optical element, the CPU that occupies rectangle 200 is making use of a program stored in ROM 202. ROM 202 also contains the calibration parameters $\alpha$, $\beta$, etc. that are necessary to convert the raw occultation information into lens parameters.

It is apparent that the calibration constants $\alpha$, $\beta$, etc. are functions of the total geometry of the instrument (lens meter, ophthalmometer, etc.) that is doing the measuring, in particular, the location and orientation of the moving boundary locus, and the location and orientation of the optical train. Also, a greater number of constants may by required to define certain configurations (e.g. ophthalmometer having four measuring apertures). However, the various elements that go into making a finished optical instrument cannot easily be assembled to precise design tolerances. As an example, with reference to FIG. 2a, lens 334 may well be displaced from its design position 334' shown in dashed outline. Additionally, the four apertures in aperture plate 332 may not be in a precise square, the shaft of rotating disc L may not be in its center, and any other of the elements may be displaced from its design position. Thus, the optical calibration constants $\alpha$, $\beta$, etc. that correspond to an instrument that has all its elements in their precise design locations will in general not provide the best output values of lens parameters since a given instrument is not likely to have its elements precisely registered. It is in recognition of this fact that the calibration procedure of the present invention set forth herein was developed.

THE CALIBRATION PROCESS

Before the optical instrument (e.g. lens meter) is capable of generating optical parameters from occulation information, the dedicated computer must be supplied with the calibration constants α, β, etc. FIG. 5 shows the electronic circuitry that is used during the calibration step to provide a set of optical constants for a particular instrument. It cannot be over-emphasized that the procedure described herein for generating the optical constants does not rely on a precision alignment of the optical elements within the instrument being calibrated. Rather, so long as the elements have been assembled with reasonable precision, such as that achievable by relatively unskilled but careful workers, the calibration procedure results in an instrument whose overall performance is comparable to the performance of one that has been assembled with great precision.

The instrument itself has the electronic components shown in FIG. 5, except that the elements within dashed rectangle 230 are not present, and the block shown as blank rectangle 200 contains a CPU in the form of an MPU chip. Rectangle 230 contains the elements of the calibration computer, and for clarity, the same reference numerals as are used for the physical components themselves in FIG. 1 are used in the schematic of FIG. 5. Thus, calibration computer 30 communicates to the instrument being calibrated, and in particular to the MPU socket 200 (analogous to MPU socket 55 in FIG. 1) by a signal buffer 75. Calibration computer 30 has its own peripherals including dual disc drive 32, printer 37, ROM mapper 35, and display terminal 40. A particular configuration will be described in a separate section entitled "The Calibration Program".

During the calibration phase, calibration computer 30 emulates the instrument's own dedicated computer which is temporarily disconnected. One portion of the program inside the calibration computer 30 is an emulator which, in conjunction with signal buffer 75, provides signals to the instrument that have similar effect to signals generated by the instrument's own CPU when in place. Thus, the instrument is under the control of calibration computer 30. During the calibration phase, calibration computer 30 does not access the instrument's memory comprising ROM 202 and RAM 204, but rather uses its own disc drive 32 or ROM capacity to perform the memory functions. (In fact, as discussed above, ROM 202 is not inserted until after the calibration process is complete.)

Broadly, the calibration procedure involves the insertion of a series of test optical elements within the sampling interval 17 of instrument 15 being calibrated. The deflections caused by these elements, or more strickly speaking, the occultation times generated by the moving boundary locus, are measured and made available to calibration computer 30. The operating system for calibration computer 30 allows the calibration program to communicate with the operator through control console 40. In particular, a series of instructions to the operator are displayed on the screen of control console 40. A typical sequence of instructions, to be followed by operator 100 once an instrument is connected to calibration computer 30, includes the following:

"Insert 'no lens' and type a space."

"Place calibration lens stand over lens head. Place calibration prism on stand with No. 1 edge flush against lens table and type a space."

"Rotate prism so that No. 2 edge is flush against lens table and type a space."

"Rotate prism so that No. 3 edge is flush against lens table and type a space."

"Rotate prism so that No. 4 edge is flush against lens table and type a space."

"Remove the calibration prism and place the ten diopter calibration sphere lens on the stand and type a space."

It should be understood that when the operator complies with each instruction and signifies his compliance by typing a space, calibration computer 30 receives the deflection information that is generated with the particular test element, or lack of a test element, in place. Once all these steps have been complied with, the mathematical portion of the calibration program within calibration computer 30 is able to manipulate the measurements thus received, and generate a set of optical calibration constants for the instrument being calibrated.

Broadly, the calibration computations are the inverse of the computations carried out by the calibrated instrument (as described at length above). Thus, measurements are made wherein the optical properties of the suspect elements are known, but the various scale factors, points of origin, angular corrections, and the like, are not known, but rather are to be determined.

First, occultation information is taken where no suspect element is in the sampling interval (i.e. null element information). Thus, no deflection is expected to occur.

Second, the prism is placed in the sampling interval and occultation information recorded. The prism is then rotated through a known angle, e.g., 90° or 180°, and further occultation information generated. On the basis of the prism and null element occultation information, it is possible to compute the points of origin and scale factors that allow a transformation of raw occultation information to beam deflections. Moreover, the relative angle between the coordinate system of the lens table and that defined by the sampling apertures can be computed.

Third, occultation information is taken with a test element having known spherical power. The knowledge that circular astigmatism of the test element must be zero is exploited. In particular, the parameters that have been computed in the above steps do not guarantee that circular astigmatism is zero for those measurements. However, it is possible by rotating the coordinate system to insure that the circular astigmatism vanishes. The rotation effectively corrects for any misalignment of the sampling apertures. This rotational correction is applied to the scale factors and points of origin that have been computed on the basis of the prism and null element occultation information.

Fourth, the spherical scale factor is computed. Corrected deflections (using the corrected constants) are computed for the sphere and null elements. The corrected sphere deflections relative to the corrected null element deflections give rise to a spherical equivalent which can then be divided into the known spherical power of the test element to provide the scale factor.

Fifth, the points of oritin for sphere and cross cylinder are computed in the basis of the corrected deflections computed on the basis of null element occultation information.

The calibration constants thus generated, along with the program required to transform raw occultation measurements into desired optical parameters (i.e. to carry out the mathematical calculations discussed above under the subheading "Operation of the Calibrated Instrument") are then written into a ROM which has been placed in ROM mapper 35. A hard copy of the optical calibration constants is also written out by printer 37 to provide a permanent record, as well as to make it possible to discover any bizarre results that the program is unable to analyze. The calibration computer is then disconnected from the instrument being calibrated (i.e. plug 77 is removed), an MPU is placed in the MPU socket, and the mapped ROM is placed in the ROM socket. The instrument has then been calibrated. A variation on this procedure of substituting CPU's is to substitute ROM's so that the calibration program is run under the control of the dedicated computer's CPU. This would be done by removing the ROM containing the operating program and inserting a ROM containing the calibration program. (Alternatively, the calibration program could be permanently resident along with the operating program.) The generated constants would be written on the instrument's own printer 212 and manually inserted into a ROM which would then be inserted into the instrument.

Having discussed the calibration procedure generally, and further having outlined the mathematical significance of the optical calibration constants $\alpha$, $\beta$, etc., it is now possible to discuss the mathematical computations that must be carried out to derive the optical calibration constants from the raw occultation measurements taken with the test elements in place. For simplicity, the discussion of the mathematics that follows is based on a simplified but nevertheless viable calibration procedure in which the prism deflections are measured for only two test prism orientations, rather than the four orientations alluded to in the discussion of the instructions to the operator.

First, occultations occurring with no test element in place are measured. Each of the four sampling apertures gives rise to an $f_i$ and a $g_i$ ($i=1,2,3,4$) as defined in equations 1 and 2. These are summed to generate an $f_O$ and $g_O$ defined as follows:

$$f_0 = \sum_{i=1}^{4} f_i/4 \tag{12a}$$

$$g_0 = \sum_{i=1}^{4} g_i/4 \tag{12b}$$

where $f_i$ and $g_i$ in this equation refer to the quantities measured with no test elements in place. Recalling the relationship between $\phi_i$ and $g_i$ from equation 4b, one can define $\phi_O$ as follows:

$$\phi_0 = \sum_{i=1}^{4} \phi_i/4 \tag{13}$$

where $\phi_O$ is related to $g_O$ as follows:

$$\phi_O = \gamma\, g_O = \delta \tag{14}$$

One parameter that is very well known and does not have to be determined from the calibration is $\gamma$, since it is the angular scale factor determined from the properties of the outer region 120 of rotating boundary locus disc L. For the measurement with no test element in place, $\phi_O$ can be set to zero, thereby allowing $\delta$ to be solved for. It is also convenient to set $Y_O = O$.

A test element having $\Delta$ prism diopters with a base direction at an orientation $\theta_+$ relative to the x axis is then inserted. A series of $f_i$ and $g_i$ are generated, and new quantities $f_+$ and $g_+$ are defined as follows:

$$f_+ = \sum_{i=1}^{4} f_i/4 \tag{15a}$$

$$g_+ = \sum_{i=1}^{4} g_i/4 \tag{15b}$$

Similarly, the measurements are taken with the prism rotated by 90°, to generate quantities $f_-$ and $g_-$ defined as follows:

$$f_- = \sum_{i=1}^{4} f_i/4 \tag{16a}$$

$$g_- = \sum_{i=1}^{4} g_i/4 \tag{16b}$$

In terms of $g_+$ and $g_-$, one obtains the average azimuthal deflections $\phi_+$ and $\phi_-$ as follows:

$$\phi_+ = \gamma\, g_{30} + \delta \tag{17a}$$

$$\phi_- = \gamma\, g_{31} + \delta \tag{17b}$$

At this point, it is possible to solve for $\alpha$, $\beta$, A, and $x_O$, expliting the fact that the measurements were generated with prism orientations that were exactly 90° apart. Thus, independent of any knowledge of the prism strength, $\xi$, defined as the ratio of $\beta$ over $\alpha$ is given by:

$$\xi = \frac{f_+ - \eta f_-}{\eta - 1} \tag{18}$$

where $\eta$ is given by:

$$\eta = \frac{\cos(\phi_+ - \phi_-) \pm \sqrt{\cos^2(\phi_+ - \phi_-) - \cos 2\phi_+ \cos 2\phi_-}}{\cos 2\phi_+} \tag{19}$$

with the relative sign taken as $+$ when $f_+ > f_-$ and $-$ when $f_- > f_{30}$.

The prism strength is then used to solve for $\alpha$ and $\beta$ absolutely as follows:

$$\alpha = \frac{\Delta/4}{\sqrt{\sin^2\phi_+\,(f_+ + \xi)^2 - \sin^2\phi_-\,(f_- + \xi)^2}} \tag{20a}$$

$$\beta = \alpha\xi \tag{20b}$$

A, the relative angle between the coordinate system in which the calculation has progressed up to this point and the lens table coordinate system is given by:

$$A = \sin^{-1}[4(\alpha\, f_+ + \beta)(\sin\phi_+)/\Delta] - \theta_+ \tag{21}$$

and $x_O$ is given by:

$$x_O = \alpha\, f_O + \beta \tag{22}$$

Thus, it can be seen that the parameters $\alpha$, $\beta$, $\gamma$, $\delta$, A, $x_O$, and $Y_O$ which give the geometrical scale factors and points of origin have been obtained solely by using null element and prism information.

The additional information required to complete the calibration computation is found in the deflections generated when a test element having spherical power D is inserted. With this lens in place, an x–y deflection for each of the four sampling areas is generated, the calculation of each $x_i$ and $y_i$ being carried out according to equations 1–5. However, the $x_i$ and $y_i$ values thus calculated will generally give a non-zero value for the circular astigmatism CA defined in Equation 8a. This indicates the presence of a non-toric surface while the test element is known not to possess such a characteristic. In order to remove this effect, it is necessary to rotate the coordinate system by an angle $\theta_s$ where:

$$\tan \theta_s = \frac{(+x_1 + x_2 - x_3 - x_4 - y_1 + y_2 + y_3 - y_4)}{-x_1 + x_2 + x_3 - x_4 - y_1 - y_2 + y_3 + y_4} \quad (23)$$

and where the solution of $\theta_s$ near $-90°$ is taken.

The already calculated values for $x_O$, $y_O$, $\delta$, and A must now be rotated by the angle $\theta_s$ to give a corresponding set of primed variables as follows:

$$x_O' = \cos(-\theta_s) \quad (24a)$$

$$y_O' = x_O \sin(-\theta_s) \quad (24b)$$

$$\delta' = \delta - \theta_s \quad (24c)$$

$$A' = A - \theta_s \quad (24d)$$

Since this is a rotation about the original origin (derived with zero prism), the prism points are still intact. Note also that $\alpha$ and $\beta$ are invariant with respect to this rotation.

Using $x_0'$, $y_0'$, $\delta$, and A', the values for $x_i$ and $y_i$ are recomputed. Additionally, $x_{0i}$ and $y_{0i}$ are commputed from the $f_i$ and $g_i$ that were generated with no test element in place. The spherical scale factor S is then given by:

$$S = D/[(-x_1 + x_2 + x_3 - x_4 - y_1 - y_2 + y_3 + y_4) - (-x_{01} + x_{02} + x_{03} - x_{04} - y_{01} - y_{02} + y_{03} + y_{04})] \quad (25)$$

The values of $Z_s$, $Z_{c+}$, and $Z_{cx}$ can now be computed, being simply the values of sphere and cross-cylinder astigmatism that result when the other parameters are applied to the $x_{0i}$ and $y_{0i}$—that is, the the computed deflections arising where no sphere or cross-cylinder astigmatism is in the system. These parameters are given as follows:

$$Z_s = S(-x_{01} + x_{02} + x_{03} - x_{04} - y_{01} - y_{02} + y_{03} + y_{04}) \quad (26a)$$

$$Z_{c+} = S(+x_{01} - x_{02} - x_{03} + x_{04} - y_{01} - y_{02} + y_{03} + y_{04}) \quad (26b)$$

$$Z_{cx} = S(+x_{01} + x_{02} - x_{03} - x_{04} + y_{01} - y_{02} - y_{03} + y_{04}) \quad (26c)$$

A refinement on the last step is to make $Z_{c+}$ and $Z_{cx}$ mildly linear in spherical equivalent since a small amount of cross-cylinder does tend to show up when suspect optics having a heavy sphere component are put in. The main source of this effect is irregularity of the sampling apertures.

The vertex correction $d_1$ is obtained by measurement of a second sphere test element of D' diopters. In the preferred embodiment D is approximately $+10$ diopters and D' is approximately $-10$ diopters. Under circumstances where the powders are approximately equal in magnitude and opposite in sign, $d_1$ is approximately given by:

$$d_1 = [(M + M') = (D + D')]/(2D^2) \quad (27)$$

where M and M' are the measured sphere powers for the test elements of known power D and D', respectively. A corrected scale factor S' is given by:

$$S' = \frac{D - D'}{M - M'} S \quad (28)$$

The constants $\alpha, \beta$, etc. thus computed are basically unique to the particular instrument being calibrated. As described above, these customized constants are written into a ROM which then becomes part of the instrument. It is the instrument's actual response, not its precise configuration, that is the basis of the computation. Thus, a precision alignment of components within the instrument is not required.

The Calibration Program

As discussed above, the calibration computer system performs two basic functions. First, it accesses the lens meter's internal registers and produces an array of numbers corresponding to raw occultation times. This is basically timing and formatting wherein the computer acts as an input/output device for reading out raw data. Second, once the raw data is read out, the calibration computer system performs the mathematical manipulations and calculations described in detail above. Once the constants are generated, they are written into a memory for placement into the calibrated instrument.

It will be evident to one skilled in the art that there exists broad latitude in choosing an interrogating and calibrating computer system. As a concrete example, the particular components of the presently used system are as follows: Microcomputer 30 is an Intel MDS-800 "Intellec" microcomputer manufactured by Intel Corporation, Santa Clara, California. Disc drive 32 is an Intel MDS-2DS dual diskette drive unit. Memory mapper 35 is an Intel UPP-101 universal PROM programmer with a UPP-878 personality card (for a 2708 ROM). Printer 37 is an Intel MSD-PRN matrix printer. Display console 40 is a Lear-Siegler ADM-3A interactive display terminal manufactured by Lear-Siegler, Anaheim, California. Signal buffer 75 is an Intel MDS-80-ICE signal buffer.

While such a computer system would be suitable for performing both the interrogating and calibrating operations, an interim hybrid system more suitable for development and testing, has been used to date. In the hybrid system, the above-described computer system is used solely to interrogate the lens meter undergoing calibration and to extract binary numbers from the instrument hardware. Sixteen binary numbers are placed in an ordered array, converted to decimal, and written on the screen of display console 40. These numbers are then manually keyboarded into a programmed HP-97 programmable calculator manufactured by Hewlett-Packard Corporation, Palo Alto, California. The reason for using such a hybrid system is that the calibration operation is essentially mathematical in nature, and is more quickly and easily programmed into a calculator than a microcomputer, at least for development purposes where the operation does not have to be totally automatic.

With this interim hybrid system, there is no prompting for placement of test elements, but rather the programmable calculator stops at various times during execution of the calibration procedure, awaiting the input of occultation times from the different test elements. The operator is responsible for ensuring that the test elements are placed in the proper sequence.

Once the calibration constants have been generated, they are printed out by the programmable calculator. In order to write these constants into the ROM for insertion into the calibrated lens meter, the constants are manually entered via display console 40 under the control of standard operating programs for the Intel MDS-800 microcomputer system. These control programs are stored on discs, and are supplied by the manufacturer with disc drive 32. The floppy disc monitor program is designated ISIS-II; the program for controlling the memory mapper is designated UPM.

The actual microcomputer code and the programmable calculator code are set forth in appendices below.

Appendix A is microcommputer code for extracting binary numbers from the instrument hardware, basically timing and formatting operations. This portion of the program puts sixteen binary numbers extracted from the instrument undergoing calibration into an ordered array.

Appendix B is microcomputer code for converting these binary numbers to decimal and writing them on the screen of display console 40.

Appendix C is programmable calculator code for performing the mathematical computations of the calibration procedure.

It should be understood that, in a final system, these various programs would be consolidated within a single computer system, and further that the computer system would not necessarily have to be as elaborate as the one set forth above.

```
LOC  OBJ        SEQ        SOURCE STATEMENT

1 ;********************************************************
                2 ;
                3 ;            LENS METER DATA ACQUISITION PACKAGE
                4 ;
                5 ;********************************************************
                6 ;
                7 ;      PROGRAM NAME:  LMDATA.ASM
                8 ;      AUTHOR:        J. COREMAN 6/20/77
                9 ;
               10 ; RECENT EDIT HISTORY....
               11 ;      4/12/78 JEC     DATA INPUT BUG?
               12 ;      2/2/78  JEC     RESET THRESHOLDS AT 720 DEGREES
               13 ;      12/29/77 JEC    ...0.3?
               14 ;      12/23/77 JEC    MORE TUNING...REV 0.2
               15 ;      12/21/77 JEC    JAZZ UP FOREGROUND REQUEST FLAG LOGIC
               16 ;      12/19/77 JEC    CHANGE ERROR FLAG
               17 ;      12/12/77 JEC    ADD FOREGROUND
               18 ;      11/30/77 JEC    MOVE ERROR FLAG
               19 ;      11/21/77 JEC    SET ERROR FLAG PROPERLY
               20 ;      9/14/77  JEC    ANOTHER SCREAMING YELLOW BUG
               21 ;      9/13/77  JEC    ADD WAIT ROUTINE, CHANGE DTMFR
               22 ;      8/15/77  JEC    OVERHAUL
               23 ;      7/12/77  JEC    SET THRESHHOLDS UNDER INTERRUPT
               24 ;      6/23/77  JEC    A BUGS??
               25 ;      6/21/77  JEC
               26 ;      6/20/77  JEC    CONVERTED FROM LMPRO
               27         NAME LMDATA
               28 ;
               29 ;
               30 ;
               31 ;
               32 ;
               33 ;
               34 ; DEFINITIONS...
               35
0001           36         BIT0    EQU     00000001B
0002           37         BIT1    EQU     00000010B
0004           38         BIT2    EQU     00000100B
0008           39         BIT3    EQU     00001000B
0010           40         BIT4    EQU     00010000B
0020           41         BIT5    EQU     00100000B
0040           42         BIT6    EQU     01000000B
```

```
LOC  OBJ       SEQ         SOURCE STATEMENT 0080           43          BIT7     EQU    10000000B
               44 ;
               45 ; DEVICE REGISTERS...
               46 ;
0080           47          DTACTR   EQU    80H     ;DETECTOR "A" COUNTER
0081           48          DTBCTR   EQU    81H     ;DETECTOR "B" COUNTER
0082           49          DTCCTR   EQU    82H     ;DETECTOR "C" COUNTER
0083           50          DTDCTR   EQU    83H     ;DETECTOR "D" COUNTER
0085           51          FCOUNT   EQU    85H     ;FINE COUNT
0084           52          FLAGS    EQU    84H     ;FLAG REGISTER
0086           53          MRKCTR   EQU    86H     ;MARK COUNT REGISTER
               54
0040           55          KBDREG   EQU    40H     ;KEYBOARD REGISTER
0020           56          DSPCTR   EQU    20H     ;DISPLAY COUNTER
0011           57          VAREG    EQU    11H     ;8251 STATUS REGISTER
0010           58          VADATA   EQU    10H     ;8251 DATA REGISTER
               59 ;
               60 ; OUTPUT DEFS...
               61 ;
0080           62          THREG    EQU    80H     ;THRESHOLD SET REGISTER
0040           63          ANCTR    EQU    40H     ;ANNUNCIATOR (ADD GROUP CODE)
0047           64          LMPREG   EQU    47H     ;MAIN LAMP CONTROL
0020           65          NUMDSP   EQU    20H     ;NUMERIC DISPLAY OUTPUT
0008           66          ICREG    EQU    08H     ;INTERRRUPT CONTROLLER
               67 ;
               68 ;OTHER DEFS...
               69 ;
               70          EXTRN    REG1, REG0
               71          EXTRN    FGDENF, FGRFLG
               72          PUBLIC   DETACQ, DETXFR, DETCON, DETCHK, DETOFF, DETHT
               73          PUBLIC   CNTERR, FGDREQ, FGDDLY
               74
               75 $ EJECT
               76 ;        DATA SPACE...
               77 ;
               78          DSEG
0000 00        79 CONFLG:  DB       0       ;1 = CONTINUOUS READ (LAYOUT MODE)
0001 00        80 DETRDY:  DB       0       ;DETECTOR READY FLAG
0002 00        81 CNTERR:  DB       0       ;1 = NOT 16 INTERRUPTS
0003 00        82 FGDREQ:  DB       0       ;FOREGROUND REQUEST FLAG
0004 00        83 FGDDLY:  DB       0       ;DELAY FOR THE ABOVE
0005 00        84 XFRFLG:  DB       0       ;SET TO 0 WHEN DATA ACCESS FINISHED
0006 00        85 DETENA:  DB       0       ;SET TO 1 TO ALLOW DATA INTERRUPTS
0007 00        86 IDXFLG:  DB       0       ;INDEX SEQUENCE FLAG, 0 = IDLE
               87
               88 ; DETECTOR BUFFERS...LOCATED AT END OF RAM...
               89
0002           90 DTPTR:   DS 2     ;POINTER TO DETECTOR A DATA
0001           91 DTCTR:   DS 1     ;DATA COUNTER...(SHOULD BE 4 * 4 = 16)
               92
               93 ;DATA BUFFER...4*4*4 BYTES
               94
0030           95 DTBUF:   DS 48
0030           96 DTXBUF:  DS 48    ;DATA SCRATCH BUFFER (FOR INTERRUPTS)
               97
               98 ; INTERRUPT VECTORS
               99 ;
               100         ASEG
               101
0008           102         ORG 08H          ;RESTART 1
```

```
LOC  OBJ          SEQ       SOURCE STATEMENT

0008 F5           103            PUSH PSW
0009 C5           104            PUSH B
000A D5           105            PUSH D
000B E5           106            PUSH H
000C C37200  C    107            JMP IDXINT
                  108
0010              109            ORG 10H           ;RESTART 2
0010 F5           110            PUSH PSW
0011 C5           111            PUSH B
0012 D5           112            PUSH D
0013 E5           113            PUSH H
0014 C33201  C    114            JMP DETINT
                  115            CSEG
                  116
                  117  $ EJECT
                  118  ;    FRONT END OF DATA ACQUISITION...
                  119  ;    INITIATE A NORMAL READ...SET THRESHHOLD, READ ONE SET OF VALUES...
                  120  ;
0000 AF           121  DETACQ: XRA A             ;A ZERO
0001 210000  D    122  DETA02: LXI H,CONFLG      ;POINT TO FIRST FLAG
0004 0E07         123            MVI C,7
0006 77           124  DETA04: MOV M,A           ;STORE CONFLG (OR ZERO)
0007 AF           125            XRA A
0008 23           126            INX H
0009 0D           127            DCR C
000A C20600  C    128            JNZ DETA04
000D 3601         129            MVI M,1          ;SET INDEX FLAG TO 1
000F C9           130            RET
                  131  ;
                  132  ;INITIATE CONTINUOUS MODE...
                  133  ;
0010 3E01         134  DETCON: MVI A,1
0012 C30100  C    135            JMP DETA02
                  136  ;
                  137  ;SHUT OFF CONTINUOUS MODE...
                  138  ;
0015 AF           139  DETOFF: XRA A
0016 320700  D    140            STA IDXFLG
0019 D347         141            OUT LMPREG
001B C9           142            RET
                  143  ;
                  144  ; CHECK DETECTOR DATA...RETURN AC = 1 IF READY, ZERO IF NOT
                  145  ;
001C 3A0100  D    146  DETCHK: LDA DETRDY
001F B7           147            ORA A
0020 C9           148            RET
                  149  ;
                  150  ;WAIT FOR DATA FLAG...
                  151  ;
0021 CD1C00  C    152  DETWT:  CALL DETCHK
0024 CA2100  C    153            JZ DETWT
0027 C9           154            RET
                  155  $ EJECT
                  156  ;TRANSFER DETECTOR DATA FOR CHANNEL IN REG (C) TO GENERAL
                  157  ;REGISTERS STARTING AT (E)...
                  158  ;
                  159  ;
0028 CD2100  C    160  DETXFR: CALL DETWT
002B C5           161            PUSH B           ;SAVE CHANNEL#
002C 21FCFF  E    162            LXI H,REG1-4
002F 78           163            MOV A,B          ;REGISTER #
```

```
LOC  OBJ        SEQ       SOURCE STATEMENT 0030 07         164       RLC              ;4 BYTES PER REGISTER...
0031 07         165       RLC
0032 5F         166       MOV E,A
0033 1600       167       MVI D,0
0035 19         168       DAD D            ;POINT H,L TO FIRST REGISTER
0036 79         169       MOV A,C          ;CHANNEL #
0037 07         170       RLC              ;TIMES 2
0038 81         171       ADD C
0039 07         172       RLC              ;X 6
003A 07         173       RLC              ;X 12 BYTES PER CHANNEL
003B 4F         174       MOV C,A          ;TO B,C
003C 0600       175       MVI B,0
003E EB         176       XCHG
003F 21FFFF  D  177       LXI H,DTBUF-12
0042 09         178       DAD B
0043 EB         179       XCHG             ;NOW D,E POINT TO DATA BUFFER, H,L TO REGISTERS
0044 0E04       180       MVI C,4          ;4 VALUES TO BE TRANSFERRED
0046 C5         181 XFRLP: PUSH B          ;SAVE COUNT
0047 E5         182       PUSH H           ;AND REGISTER POINTER
0048 EB         183       XCHG             ;DATA POINTER TO H,L
0049 46         184       MOV B,M          ;FINE COUNT
004A 23         185       INX H
004B 0E00       186       MVI C,0          ;LOWER BYTE ZERO
004D 5E         187       MOV E,M          ;TOTAL COUNT
004E 23         188       INX H
004F 1600       189       MVI D,0          ;UPPER BYTE ZERO
0051 E5         190       PUSH H           ;SAVE DATA POINTER
0052 CD9001  C  191       CALL DIV8        ;DIVIDE FINE COUNT BY TOTAL (TO H,L)
0055 D1         192       POP D            ;GET DATA POINTER TO D,E
0056 1A         193       LDAX D           ;GET COURSE COUNT
0057 13         194       INX D
0058 84         195       ADD H            ;ADD COURSE COUNT TO MSB OF ADJUSTED FINE COUNT
0059 4D         196       MOV C,L
005A E1         197       POP H            ;REGISTER POINTER
005B 3600       198       MVI M,0          ;POSITIVE SIGN BYTE
005D 23         199       INX H
005E 71         200       MOV M,C          ;LOW BYTE
005F 23         201       INX H
0060 77         202       MOV M,A          ;HI BYTE
0061 23         203       INX H
0062 3600       204       MVI M,0          ;ZERO EXP
0064 23         205       INX H
0065 C1         206       POP B            ;RESTORE COUNT
0066 0D         207       DCR C
0067 C24600  C  208       JNZ XFRLP
006A C1         209       POP B            ;GET CHANNEL#
006B 79         210       MOV A,C
006C D604       211       SUI 4
006E 320500  D  212       STA XFRFLG       ;SET LOCKOUT FLAG NON-ZERO UNLESS CHANNEL = 4
0071 C9         213       RET
                214 $ EJECT
                215 ;     MARK TRACK INTERRUPT...HAPPENS EVERY 90 DEGREES.
                216 ;     IF THE FLAG IS NON-ZERO THEN DISPATCH ON IT...
                217 ;     STEPPING THROUGH A SEQUENCE OF EVENTS RELATED TO DISC ROTATION.
                218 ;
                219 IDXINT: ;PUSH PSW       ;SAVE REGISTERS
                220        ;PUSH B
                221        ;PUSH D
                222        ;PUSH H
0072 DB06       223       IN MRKCTR        ;GET MARK COUNT
0074 4F         224       MOV C,A          ;TO REGISTER C
```

```
LOC  OBJ         SEQ         SOURCE STATEMENT 0075 3A0700  D   225             LDA  IDXFLG      ;GET FLAG
0078 B7          226             ORA  A           ;CHECK FOR ZERO (= IDLE)
0079 CA2C01  C   227             JZ   IDXIGN      ;ZERO FLAG, IGNORE INTERRUPT
007C E607        228             ANI  7           ;MASK FLAG (8 BECOMES ZERO)
007E 07          229             RLC              ; TIMES TWO
007F 5F          230             MOV  E,A         ;TO D,E
0080 1600        231             MVI  D,0
0082 218B00  C   232             LXI  H,IDXTBL    ;TABLE BASE
0085 19          233             DAD  D
0086 5E          234             MOV  E,M         ;GET DISPATCH ADDRESS
0087 23          235             INX  H
0088 56          236             MOV  D,M
0089 EB          237             XCHG             ;TO H,L
008A E9          238             PCHL             ;DISPATCH
                 239 ;
                 240 ;DISPATCH TABLE...
                 241 ;
008B DE00    C   242 IDXTBL: DW  IDX720          ;0 = DISABLE (720 DEGREES)
008D 9B00    C   243         DW  IDX90           ;1 = 90 DEGREES
008F A301    C   244         DW  IDX180
0091 A300    C   245         DW  IDX270
0093 AF00    C   246         DW  IDX360
0095 C900    C   247         DW  IDX450
0097 CF00    C   248         DW  IDX540
0099 D500    C   249         DW  IDX630
                 250 $ EJECT
                 251 ;    INITIALIZE AT FLAG=1...SYNC WITH 90 DEGREES...
                 252 ;
009B 79          253 IDX90:  MOV  A,C            ;GET MARK COUNT
009C FE40        254         CPI  64             ;CHECK FOR 90 DEGREES
009E C22C01  C   255         JNZ  IDXRT2         ;IS NOT, WAIT
                 256 ;
                 257 ; 90 DEGREES...TURN LAMP ON
                 258 ;
00A1 3E01        259         MVI  A,BIT0
00A3 D347        260         OUT  LMPREG
00A5 C32801  C   261         JMP  IDXRET         ;RETURN, INCREMENTING FLAG TO 2...
                 262 ;
                 263 ; 270 DEGREES...SET LIGHT THRESHHOLD...
                 264 ;
00A8 3E40        265 IDX270: MVI  A,BIT6
00AA D380        266         OUT  THREG
00AC C32801  C   267         JMP  IDXRET
                 268 ;
                 269 ; 360 DEGREES...SET DARK THRESHOLD, INITIALIZE POINTERS AND ENABLE DETECTORS...
                 270 ;
00AF 3E04        271 IDX360: MVI  A,4
00B1 320700  D   272         STA  IDXFLG         ;SET INDEX FLAG FOR FUNNY ENTRIES
00B4 3E80        273         MVI  A,BIT7
00B6 D380        274         OUT  THREG
00B8 213B00  D   275         LXI  H,DTXBUF
00BB 220800  D   276         SHLD DTPTR          ;SET POINTER
00BE AF          277         XRA  A
00BF 320A00  D   278         STA  DTCTR          ;CLEAR COUNTER
00C2 3C          279         INR  A
00C3 320600  D   280         STA  DETENA         ;SET ENABLE FLAG
00C6 C32801  C   281         JMP  IDXRET
                 282 ;
                 283 ; 450 DEGREES...SET POINTER FOR SECOND SET OF VALUES...
                 284 ;
00C9 213E00  D   285 IDX450: LXI  H,DTXBUF+3
```

```
LOC  OBJ        SEQ         SOURCE STATEMENT

00CC C3D800  C  286             JMP   IDXRT3
                287 ;
                288 ;   540 DEGREES...SET POINTER FOR 3RD SET OF VALUES...
                289 ;
00CF 214100  D  290 IDX540: LXI   H,DTXBUF+6
00D2 C3D800  C  291             JMP   IDXRT3
                292 ;
                293 ;   630 DEGREES...SET POINTER TO 4TH SET..
                294 ;
00D5 214400  D  295 IDX630: LXI   H,DTXBUF+9
00D8 220800  D  296 IDXRT3: SHLD  DTPTR
00DB C32801  C  297             JMP   IDXRET
                298 ;
                299 ;   720 DEGREES...RESET ENABLE FLAG (UNLESS CONTINUOUS) AND SET DATA READY...
                300 ;
00DE 3A0500  D  301 IDX720: LDA   XFRFLG      ;CHECK TRANSFER LOCK-OUT FLAG
00E1 B7         302             ORA   A
00E2 C2AF00  C  303             JNZ   IDX360      ;SET, GO FOR ANOTHER REV
00E5 210200  D  304             LXI   H,CNTERR
00E8 3601       305             MVI   M,1         ;SET COUNT ERROR SPECULATIVELY
00EA 3A0A00  D  306             LDA   DTCTR
00ED FE10       307             CPI   16          ;CHECK COUNT
00EF C2F300  C  308             JNZ   IDX721      ;NOT 16, LEAVE ERROR FLAG SET
00F2 35         309             DCR   M           ;CLEAR FLAG
00F3 2B         310 IDX721: DCX   H
00F4 3601       311             MVI   M,1         ;SET READY FLAG
00F6 110800  D  312             LXI   D, DTBUF
00F9 213B00  D  313             LXI   H,DTXBUF
00FC 0E30       314             MVI   C,48
00FE 7E         315 IDX722: MOV   A,M         ;MOVE DATA TO REAL BUFFER
00FF 12         316             STAX  D
0100 23         317             INX   H
0101 13         318             INX   D
0102 0D         319             DCR   C
0103 C2FE00  C  320             JNZ   IDX722
0106 210400  D  321             LXI   H,FGDDLY
0109 34         322             INR   M           ;BUMP DELAY FLAG
010A 7E         323             MOV   A,M
010B 1F         324             RAR
010C D21201  C  325             JNC   IDX723      ;RUN FOREGROUND EVERY OTHER LAP
010F 2B         326             DCX   H
0110 3601       327             MVI   M,1         ;SET REQUEST
0112 3A0000  D  328 IDX723: LDA   CONFLG
0115 B7         329             ORA   A
0116 C2AF00  C  330             JNZ   IDX360      ;CONTINUOUS, LOOP FROM 360
0119 320700  D  331             STA   IDXFLG      ;RESET INDEX FLAG
011C D347       332             OUT   LMPREG      ;LAMP OFF
011E 320600  D  333             STA   DETENA      ;DISABLE DETECTOR
0121 3EC0       334             MVI   A,BIT6+BIT7
0123 D380       335             OUT   THREG       ;RESET THRESHOLDS
0125 C32C01  C  336             JMP   IDXRT2
                337 ;
                338 ;RETURN FROM INTERRUPT...
                339 ;
                340 IDX180:
0128 210700  D  341 IDXRET: LXI   H,IDXFLG
012B 34         342             INR   M           ;INCREMENT FLAG
                343 IDXIGN:
012C E1         344 IDXRT2: POP   H
012D D1         345             POP   D
012E C1         346             POP   B
```

```
LOC  OBJ         SEQ        SOURCE STATEMENT

012F F1          347        POP PSW
0130 FB          348        EI
0131 C9          349        RET
                 350 $ EJECT
                 351 ;      DETECTOR INTERRUPT DRIVER...
                 352 ;      CHECK FLAG BYTE FOR EACH DETECTOR AND CALL APPROPRIATE ROUTINE...
                 353 ;
                 354 DETINT: ;PUSH PSW    ;SAVE REGGIES .
                 355         ;PUSH B
                 356         ;PUSH D
                 357         ;PUSH H
0132 3A0600  D   358        LDA DETENA    ;CHECK DISABLE FLAG
0135 0F          359        RRC
0136 D25101  C   360        JNC DTIRT0    ;DISABLED...
0139 DB84        361        IN FLAGS      ;GET FLAG BYTE
013B 0F          362        RRC           ;DETECTOR A FLAG TO CARRY
013C DC5C01  C   363        CC DTAINT     ;SET, GO PROCESS IT
013F 0F          364        RRC           ;DET B FLAG TO CARRY
0140 DC7501  C   365        CC DTBINT
0143 0F          366        RRC           ;DET C FLAG TO CARRY
0144 DC7E01  C   367        CC DTCINT
0147 0F          368        RRC           ;DET D TO CARRY
0148 DC8701  C   369        CC DTDINT
014B E1          370 DTXRET: POP H
014C D1          371        POP D
014D C1          372        POP B
014E F1          373        POP PSW
014F FB          374        EI
0150 C9          375        RET
0151 DB80        376 DTIRT0: IN DTACTR
0153 DB81        377        IN DTBCTR
0155 DB82        378        IN DTCCTR
0157 DB83        379        IN DTDCTR
0159 C34B01  C   380        JMP DTXRET
                 381 $ EJECT
                 382 ; DETECTOR A INTERRUPT ROUTINE...GET FINE COUNT, COURSE COUNT, AND
                 383 ; TOTAL FINE COUNT AND STORE IN BUFFER...
                 384 ;
                 385 ;
015C 010000      386 DTAINT: LXI B,0      ;OUR DATA OFFSET
015F F5          387        PUSH PSW      ;PRESERVE AC
0160 DB80        388        IN DTACTR     ;GET DATA
                 389 ;
                 390 ; ENTER HERE WITH AC = FINE COUNT, B,C = DATA OFFSET
                 391 ;
0162 2A0800  D   392 DTXINT: LHLD DTPTR
0165 09          393        DAD B
0166 77          394        MOV M,A       ;STORE FINE COUNT IN BUFFER
0167 23          395        INX H
0168 DB85        396        IN FCOUNT     ;TOTAL COUNT
016A 77          397        MOV M,A       ;INTO BUFFER
016B 23          398        INX H
016C DB86        399        IN MRKCTR     ;MARK COUNT
016E 77          400        MOV M,A
016F 210A00  D   401        LXI H,DTCTR
0172 34          402        INR M         ;COUNT IT
0173 F1          403        POP PSW
0174 C9          404        RET           ;RETURN
                 405 ;
                 406 ;DETECTOR B INTERRUPT...
                 407 ;
```

```
LOC  OBJ        SEQ          SOURCE STATEMENT 0175 010C00     408 DTBINT:  LXI  B,12
0178 F5         409          PUSH PSW
0179 DB81       410          IN   DTBCTR
017B C36201 C   411          JMP  DTXINT
                412 ;
017E 011800     413 DTCINT:  LXI  B,24
0181 F5         414          PUSH PSW
0182 DB82       415          IN   DTCCTR
0184 C36201 C   416          JMP  DTXINT
                417
0187 012400     418 DTDINT:  LXI  B,36
018A F5         419          PUSH PSW
018B DB83       420          IN   DTDCTR
018D C36201 C   421          JMP  DTXINT
                422 $ EJECT
                423 ; 8-BIT DIVIDE ROUTINE....DIVIDE B,C BY E AND RETURN QUO IN H,L
                424 ;
0190 AF         425 DIV8:    XRA  A
0191 93         426          SUB  E          ;COMPLIMENT THE DIVISOR
0192 57         427          MOV  D,A        ;TO REGISTER D OF D,E PAIR
0193 1E00       428          MVI  E,0
0195 EB         429          XCHG            ;TO H,L ... WHICH IT WILL SHARE WITH QUO.
0196 110000     430          LXI  D,0        ;CLEAR D,E
0199 D5         431          PUSH D          ;CLEAR QUO
019A 1E09       432          MVI  E,9        ;COUNTER FOR 8 BITS (+1)
                433 ;
                434 ;LOOP FOR NEXT BIT...ADD (MINUS) DIVISOR TO DIVIDEND, KEEP IT IF PLUS.
                435 ;
019C E5         436 DIV8LP:  PUSH H          ;SAVE DIVISOR
019D 09         437          DAD  B          ;SUBTRACT
019E D2A301 C   438          JNC  DIV82      ;MINUS...
01A1 44         439          MOV  B,H        ;UPDATE DIV'ND
01A2 4D         440          MOV  C,L
01A3 E1         441 DIV82:   POP  H
01A4 E3         442          XTHL            ;GET QUO
01A5 7D         443          MOV  A,L        ;SHIFT CARRY BIT IN
01A6 17         444          RAL
01A7 6F         445          MOV  L,A
01A8 7C         446          MOV  A,H
01A9 17         447          RAL
01AA 67         448          MOV  H,A
                449 ;
                450 ;NOW SHIFT DIV'ER DOWN...
                451 ;
01AB E3         452          XTHL
01AC 37         453          STC
01AD 7C         454          MOV  A,H
01AE 1F         455          RAR
01AF 67         456          MOV  H,A
01B0 7D         457          MOV  A,L
01B1 1F         458          RAR
01B2 6F         459          MOV  L,A
01B3 1D         460          DCR  E          ;DECREMENT BIT COUNT
01B4 C29C01 C   461          JNZ  DIV8LP
01B7 E1         462          POP  H
01B8 C9         463          RET
                464 $ EJECT
                465 ;   THE END....
                466          END
```

PUBLIC SYMBOLS
CNTERR D 0002   DETACQ C 0000   DETCHK C 001C   DETCON C 0010   DETOFF C 0015   DETWT C 0021   DETXFR C 0028
FGDDLY D 0004   FGDREQ D 0003

EXTERNAL SYMBOLS
FGDENF E 0000   FORFLG E 0000   REG0   E 0000   REG1   E 0000

USER SYMBOLS
ANCTR  A 0040   BIT0   A 0001   BIT1   A 0002   BIT2   A 0004   BIT3   A 0008   BIT4   A 0010   BIT5   A 0020
BIT6   A 0040   BIT7   A 0080   CNTERR D 0002   CONFLG D 0000   DETACQ C 0000   DETA02 C 0001   DETA04 C 0006
DETCHK C 001C   DETCON C 0010   DETENA D 0006   DETINT C 0132   DETOFF C 0015   DETRDY D 0001   DETWT  C 0021
DETXFR C 0028   DIV8   C 0190   DIV82  C 01A3   DIV8LP C 019C   DSPCTR A 0028   DTACTR A 0080   DTAINT C 015C
DTBCTR A 0081   DTBINT C 0175   DTBUF  D 000B   DTCCTR A 0082   DTCINT C 017E   DTCTR  D 000A   DTDCTR A 0083
DTDINT C 0187   DTIRT0 C 0151   DTPTR  D 0008   DTXBUF D 003B   DTXINT C 0162   DTXRET C 014B   FCOUNT A 0035
FGDDLY D 0004   FGDENF E 0000   FGDREQ D 0003   FLAGS  A 0034   FORFLG E 0000   ICREG  A 0008   IDX180 C 0128
IDX270 C 00A8   IDX360 C 00AF   IDX450 C 00C9   IDX540 C 00CF   IDX630 C 00D5   IDX720 C 00DE   IDX721 C 00F3
IDX722 C 00FE   IDX723 C 0112   IDX90  C 009B   IDXFLG D 0007   IDXIGN C 012C   IDXINT C 0072   IDXRET C 0123
IDXRT2 C 012C   IDXRT3 C 00D8   IDXTBL C 008B   KBDREG A 0046   LMPREG A 0047   MRKCTR A 0086   NUMDSP A 0020
REG0   E 0000   REG1   E 0000   THREG  A 0080   VADATA A 0010   VAREG  A 0011   XFRFLG D 0005   XFRLP  C 0046

ASSEMBLY COMPLETE, NO ERRORS

LOC  OBJ       SEQ        SOURCE STATEMENT

```
  1 ;****************************************************************
  2 ;
  3 ;         L.A. DATA DISPLAY PROGRAM
  4 ;
  5 ;   CONVERTS RAW DATA COUNTS FROM L.A. (CONNECTED VIA ICE-80)
  6 ;   AND DISPLAYS AS DECIMAL NUMBERS ON MDS CRT DISPLAY.
  7 ;   ASSUMES I/O BANK 0FH IS MAPPED INTO THE SAME MDS BANK.
  8 ;   ALL OTHER I/O BANKS UNGUARDED.
  9 ;
 10 ;****************************************************************
 11 ;        PROGRAM NAME:   LACRT.ASM
 12 ;        AUTHOR:         J. CORENMAN
 13 ;
 14          NAME  LACRT
 15 ;
 16 ; DEFINITIONS...
 17
0001          18     BIT0    EQU     00000001B
0002          19     BIT1    EQU     00000010B
0004          20     BIT2    EQU     00000100B
0008          21     BIT3    EQU     00001000B
0010          22     BIT4    EQU     00010000B
0020          23     BIT5    EQU     00100000B
0040          24     BIT6    EQU     01000000B
0080          25     BIT7    EQU     10000000B
              26 ;
              27 ; DEVICE REGISTERS...
              28 ;
0080          29     DTACTR  EQU     80H     ;DETECTOR "A" COUNTER
0081          30     DTBCTR  EQU     81H     ;DETECTOR "B" COUNTER
0082          31     DTCCTR  EQU     82H     ;DETECTOR "C" COUNTER
0083          32     DTDCTR  EQU     83H     ;DETECTOR "D" COUNTER
0085          33     FCOUNT  EQU     85H     ;FINE COUNT
0084          34     FLAGS   EQU     84H     ;FLAG REGISTER
0086          35     MRKCTR  EQU     86H     ;MARK COUNT REGISTER
              36
```

```
LOC  OBJ        SEQ       SOURCE STATEMENT

37 ;
                38 ; OUTPUT DEFS...
                39 ;
0080            40        THREG   EQU     80H     ;THRESHOLD SET REGISTER
                41 ;
                42 ;UNUSED VECTORS
                43        ASEG
0018            44        ORG 18H                 ;DISPLAY
0018 D320       45        OUT 20H
001A FB         46        EI
001B C9         47        RET
                48
0020            49        ORG 20H                 ;PRINTER
0020 F5         50        PUSH PSW
0021 3E80       51        MVI A,80H
0023 D308       52        OUT 8H
0025 F1         53        POP PSW
0026 FB         54        EI
0027 C9         55        RET
                56
0028            57        ORG 28H
0028 F5         58        PUSH PSW
0029 DB40       59        IN 40H
002B F1         60        POP PSW
002C FB         61        EI
002D C9         62        RET
                63
0030            64        ORG 30H                 ;SERIAL I/O
0030 F5         65        PUSH PSW
0031 AF         66        XRA A
0032 D311       67        OUT 11H
0034 F1         68        POP PSW
0035 FB         69        EI
0036 C9         70        RET
                71 $ EJECT
                72 ;FRONT END....START-UP CODE
                73
                74        ASEG
0000            75        ORG 0
                76
0000 C30000  C  77        JMP START
                78
                79        DSEG
0032            80        DS 50
0002            81 STCK:  DS 2
                82
                83        CSEG
                84
0000 213200  D  85 START: LXI SP,STCK
0003 21001C     86        LXI H,1C00H
0006 010004     87        LXI B,0400H
0009 3600       88 CLRLP: MVI M,0
000B 23         89        INX H
000C 0D         90        DCR C
000D C20900  C  91        JNZ CLRLP
0010 05         92        DCR B
0011 C20900  C  93        JNZ CLRLP
0014 FB         94        EI
                95 ;
0015 CDB000  C  96        CALL DETACQ     ;STAART DATA
                97 ;
```

```
LOC  OBJ        SEQ     SOURCE STATEMENT

98 ;OUTPUT LOOP...CLEAR SCREEN AND START OUTPUT
                99 ;
0018 01A000  C  100 LOOP:   LXI B,CLRST
001B CD3800  C  101         CALL STOUT
001E 3A5500  D  102         LDA CNTERR      ;CHECK FOR COUNT ERROR
0021 B7        103         ORA A
0022 CA2B00  C  104         JZ LOOP1
0025 01A200  C  105         LXI B,ERRST
0028 CD3800  C  106         CALL STOUT      ;OUTPUT "ERROR"
002B 019F00  C  107 LOOP1:  LXI B,CRLF
002E CD3800  C  108         CALL STOUT
0031 CDCE00  C  109         CALL DETXFR     ;TRANSFER DATA
0034 1E10     110         MVI E,16
0036 219C00  D  111         LXI H,DTREG     ;POINTER TO DATA NUMBERS
                112 ;
                113 ;SMALL LOOP...OUTPUT NEXT NUMBER
                114 ;
0039 4E       115 LOOP2:  MOV C,M
003A 23       116         INX H
003B 46       117         MOV B,M
003C 23       118         INX H
003D D5       119         PUSH D
003E E5       120         PUSH H
003F CD5100  C  121         CALL DNOUT
0042 019F00  C  122         LXI B,CRLF
0045 CD3800  C  123         CALL STOUT
0048 E1       124         POP H
0049 D1       125         POP D
004A 1D       126         DCR E
004B C23900  C  127         JNZ LOOP2
004E C31800  C  128         JMP LOOP
                129 $EJECT
                130 ;CONVERT NUMBER IN B,C TO DECIMAL DIGIT STRING
                131 ;
0051 218100  C  132 DNOUT:  LXI H,FCTTBL    ;POINT TO TABLE OF (NEG) FACTORS
0054 E5       133         PUSH H
0055 60       134         MOV H,B         ;NUMBER TO H,L
0056 69       135         MOV L,C
0057 E3       136 DNOLP:  XTHL            ;GET FACTOR POINTER
0058 4E       137         MOV C,M         ;GET IT
0059 23       138         INX H
005A 46       139         MOV B,M
005B 23       140         INX H
005C E3       141         XTHL            ;GET NUMBER AGAIN
005D 0C       142         INR C
005E CA7300  C  143         JZ DNOUT2       ;-1 MEANS DONE
0061 0D       144         DCR C
0062 AF       145         XRA A           ;DIGIT=0
0063 54       146 DNOLP2: MOV D,H         ;SAVE NUMBER
0064 5D       147         MOV E,L
0065 3C       148         INR A
0066 09       149         DAD B
0067 DA6300  C  150         JC DNOLP2       ;CARRY MEANS OK
006A 3D       151         DCR A           ;UNDERFLOW...DIGIT TOO BIG
006B 62       152         MOV H,D         ;RESTORE NUMBER
006C 6B       153         MOV L,E
006D CD7900  C  154         CALL DIGOUT
0070 C35700  C  155         JMP DNOLP
0073 7D       156 DNOUT2: MOV A,L         ;GET REMAINDER
0074 CD7900  C  157         CALL DIGOUT
0077 E1       158         POP H
```

```
LOC  OBJ         SEQ      SOURCE STATEMENT

0078 C9          159          RET
                 160   ;
                 161   ;OUTPUT A DIGIT
                 162
0079 C630        163   DIGOUT: ADI '0'
007B E5          164          PUSH H
007C CD9500   C  165          CALL CHOUT
007F E1          166          POP H
0080 C9          167          RET
0081 F0D8        168   FCTTBL: DW -10000, -1000, -100, -10, -1
0083 18FC
0085 9CFF
0087 F6FF
0089 FFFF
                 169   $EJECT
                 170   ;STRING OUTPUT...
                 171   ;
008B 0A          172   STOUT:  LDAX B
008C 03          173          INX B
008D B7          174          ORA A
008E C8          175          RZ
008F CD9500   C  176          CALL CHOUT
0092 C38B00   C  177          JMP STOUT
                 178
                 179   ;CHARACTER OUTPUT...
                 180   ;
0095 D3F6        181   CHOUT:  OUT 0F6H
0097 DBF7        182   CHOUT1: IN 0F7H
0099 E601        183          ANI BIT0
009B CA9700   C  184          JZ CHOUT1
009E C9          185          RET
                 186
009F 0D          187   CRLF:   DB 0DH, 0AH, 0
00A0 0A
00A1 00
00A2 44415441    188   EPRST:  DB 'DATA ERROR', 0
00A6 20455252
00AA 4F52
00AC 00
00AD 1E          189   CLRST:  DB 1EH, 1AH, 0
00AE 1A
00AF 00
                 190   $EJECT
                 191   ;       DATA SPACE....
                 192   ;
                 193          DSEG
0034 00          194   DETRDY: DB      0       ;DETECTOR READY FLAG
0035 00          195   CNTERR: DB      0       ;1 = NOT 16 INTERRUPTS
0036 00          196   XFRFLG: DB      0       ;SET TO 0 WHEN DATA ACCESS FINISHED
0037 00          197   DETENA: DB      0       ;SET TO 1 TO ALLOW DATA INTERRUPTS
0038 00          198   IDXFLG: DB      0       ;INDEX SEQUENCE FLAG, 0 = IDLE
                 199
                 200   ; DETECTOR BUFFERS...LOCATED AT END OF RAM...
                 201
0002             202   DTPTR:  DS 2    ;POINTER TO DETECTOR A DATA
0001             203   DTCTR:  DS 1    ;DATA COUNTER...(SHOULD BE 4 * 4 = 16)
                 204
                 205   ;DATA BUFFER...4*4*4 BYTES
                 206
0030             207   DTBUF:  DS 48
0030             208   DTXBUF: DS 48   ;DATA SCRATCH BUFFER (FOR INTERRUPTS)
```

```
LOC  OBJ        SEQ        SOURCE STATEMENT 0020            209 DTREG: DS 32
                210 ;
                211 ; INTERRUPT VECTORS
                212 ;
                213         ASEG
                214
0008            215         ORG 08H         ;RESTART 1
0008 F5         216         PUSH PSW
0009 C5         217         PUSH B
000A D5         218         PUSH D
000B E5         219         PUSH H
000C C30101  C  220         JMP IOXINT
                221
0010            222         ORG 10H         ;RESTART 2
0010 F5         223         PUSH PSW
0011 C5         224         PUSH B
0012 D5         225         PUSH D
0013 E5         226         PUSH H
0014 C3A501  C  227         JMP DETINT
                228         CSEG
                229
                230 $ EJECT
                231 ;       FRONT END OF DATA ACQUISITION...
                232 ;       INITIATE A NORMAL READ...SET THRESHHOLD, READ ONE SET OF VALUES.
                233 ;
0080 213400  D  234 DETACQ: LXI H,DETRDY    ;POINT TO FIRST FLAG
0083 0E04       235         MVI C,4
0085 AF         236         XRA A
0086 77         237 DETA04: MOV M,A         ;STORE A ZERO
0087 23         238         INX H
0088 0D         239         DCR C
0089 C28600  C  240         JNZ DETA04
008C 3601       241         MVI M,1         ;SET INDEX FLAG TO 1
008E C9         242         RET
                243 ;
                244 ; CHECK DETECTOR DATA...RETURN AC = 1 IF READY, ZERO IF NOT
                245 ;
00BF 3A2400  D  246 DETCHK: LDA DETRDY
00C2 B7         247         ORA A
00C3 C9         248         RET
                249 ;
                250 ;WAIT FOR DATA FLAG..
                251 ;
00C4 CDBF00  C  252 DETWT:  CALL DETCHK
00C7 CAC400  C  253         JZ DETWT
00CA C9         254         RET
                255 $ EJECT
                256 ;TRANSFER DETECTOR DATA FOR CHANNEL IN REG (C) TO REGISTER LIST
                257 ;
00CB CDC400  C  258 DETXFR: CALL DETWT
00CE 3E01       259         MVI A,1
00D0 322500  D  260         STA XFRFLG
00D3 219C00  D  261         LXI H,DTREG
00D6 112C00  D  262         LXI D,DTBUF
00D9 0E10       263         MVI C,16        ;# VALUES TO BE TRANSFERRED
00DB C5         264 XFRLP:  PUSH B          ;SAVE COUNT
00DC E5         265         PUSH H          ;AND REGISTER POINTER
00DD EB         266         XCHG            ;DATA POINTER TO H,L
00DE 46         267         MOV B,M         ;FINE COUNT
00DF 23         268         INX H
00E0 0E00       269         MVI C,0         ;LOWER BYTE ZERO
```

```
LOC  OBJ      SEQ      SOURCE STATEMENT

00E2 5E       270      MOV E,M          ;TOTAL COUNT
00E3 23       271      INX H
00E4 1600     272      MVI D,0          ;UPPER BYTE ZERO
00E6 E5       273      PUSH H           ;SAVE DATA POINTER
00E7 CD9302 C 274      CALL DIV8        ;DIVIDE FINE COUNT BY TOTAL (TO H,L)
00EA D1       275      POP D            ;GET DATA POINTER TO D,E
00EB 1A       276      LDAX D           ;GET COURSE COUNT
00EC 13       277      INX D
00ED 84       278      ADD H            ;ADD COURSE COUNT TO MSB OF ADJUSTED FINE COUNT
00EE 4D       279      MOV C,L
00EF E1       280      POP H            ;REGISTER POINTER
00F0 71       281      MOV M,C          ;LOW BYTE
00F1 23       282      INX H
00F2 77       283      MOV M,A          ;HI BYTE
00F3 23       284      INX H
00F4 C1       285      POP B            ;RESTORE COUNT
00F5 0D       286      DCR C
00F6 C2DB00 C 287      JNZ XFRLP
00F9 AF       288      XRA A
00FA 323600 D 289      STA XFRFLG       ;SET LOCKOUT FLAG NON-ZERO
00FD 322400 D 290      STA DETRDY       ;RESET READY FLAG
0100 C9       291      RET
              292 $ EJECT
              293 ;    MARK TRACK INTERRUPT...HAPPENS EVERY 90 DEGREES
              294 ;    IF THE FLAG IS NON-ZERO THEN DISPATCH ON IT...
              295 ;    STEPPING THROUGH A SEQUENCE OF EVENTS RELATED TO DISC ROTATION
              296 ;
              297 IDXINT: ;PUSH PSW     ;SAVE REGISTERS
              298         ;PUSH B
              299         ;PUSH D
              300         ;PUSH H
0101 DB86     301      IN MRKCTR        ;GET MARK COUNT
0103 4F       302      MOV C,A          ;TO REGISTER C
0104 3A3800 D 303      LDA IDXFLG       ;GET FLAG
0107 B7       304      ORA A            ;CHECK FOR ZERO (= IDLE)
0108 CA9F01 C 305      JZ IDXIGN        ;ZERO FLAG, IGNORE INTERRUPT
010B E607     306      ANI 7            ;MARK FLAG (8 BECOMES ZERO)
010D 07       307      RLC              ;TIMES TWO
010E 5F       308      MOV E,A          ;TO D,E
010F 1600     309      MVI D,0
0111 211A01 C 310      LXI H,IDXTBL     ;TABLE BASE
0114 19       311      DAD D
0115 5E       312      MOV E,M          ;GET DISPATCH ADDRESS
0116 23       313      INX H
0117 56       314      MOV D,M
0118 EB       315      XCHG             ;TO H,L
0119 E9       316      PCHL             ;DISPATCH
              317 ;
              318 ;DISPATCH TABLE...
              319 ;
011A 6901   C 320 IDXTBL: DW  IDX720    ;0 = DISABLE (720 DEGREES)
011C 2A01   C 321         DW  IDX90     ;1 = 90 DEGREES
011E 9601   C 322         DW  IDX180
0120 3301   C 323         DW  IDX270
0122 3A01   C 324         DW  IDX360
0124 5401   C 325         DW  IDX450
0126 5A01   C 326         DW  IDX540
0128 6001   C 327         DW  IDX630
              328 $ EJECT
              329 ;   INITIALIZE AT FLAG=1...SYNC WITH 90 DEGREES...
              330 ;
```

```
LOC  OBJ        SEQ       SOURCE STATEMENT 012A 79         221 IDX90:  MOV A,C          ;GET MARK COUNT
012B FE40       222         CPI 64           ;CHECK FOR 90 DEGREES
012D C29F01  C  223         JNZ IDXRT2       ;IS NOT, WAIT
                224 ;
                225 ;  90 DEGREES...TURN LAMP ON.
                226 ;
0130 C39901  C  227         JMP IDXRET       ;RETURN, INCREMENTING FLAG TO 2...
                228 ;
                229 ; 270 DEGREES...SET LIGHT THRESHHOLD...
                230 ;
0133 3E40       241 IDX270: MVI A,BIT6
0135 D330       242         OUT THREG
0137 C39901  C  243         JMP IDXRET
                244 ;
                245 ; 360 DEGREES...SET DARK THRESHOLD, INITIALIZE POINTERS AND ENABLE DETECTORS...
                246 ;
013A 3E04       247 IDX360: MVI A,4
013C 222900  D  248         STA IDXFLG       ;SET INDEX FLAG FOR FUNNY ENTRIES
013F 3E80       249         MVI A,BIT7
0141 D330       250         OUT THREG
0143 216C00  D  251         LXI H,DTXBUF
0146 222500  D  252         SHLD DTPTR       ;SET POINTER
0149 AF        253         XRA A
014A 222800  D  254         STA DTCTR        ;CLEAR COUNTER
014D 3C        255         INR A
014E 222700  D  256         STA DETEN        ;SET ENABLE FLAG
0151 C39901  C  257         JMP IDXRET
                258 ;
                259 ; 450 DEGREES...SET POINTER FOR SECOND SET OF VALUES...
                260 ;
0154 216F00  D  261 IDX450: LXI H,DTXBUF+3
0157 C36301  C  262         JMP IDXRT3
                263 ;
                264 ; 540 DEGREES...SET POINTER FOR 3RD SET OF VALUES...
                265 ;
015A 217200  D  266 IDX540: LXI H,DTXBUF+6
015D C36301  C  267         JMP IDXRT3
                268 ;
                269 ; 630 DEGREES...SET POINTER TO 4TH SET..
                270 ;
0160 217500  D  271 IDX630: LXI H,DTXBUF+9
0163 222500  D  272 IDXRT3: SHLD DTPTR
0166 C39901  C  273         JMP IDXRET
                274 ;
                275 ; 720 DEGREES...RESET ENABLE FLAG (UNLESS CONTINUOUS) AND SET DATA READY...
                276 ;
0169 3A2600  D  277 IDX720: LDA XFRFLG       ;CHECK TRANSFER LOCK-OUT FLAG
016C B7        278         ORA A
016D C23A01  C  279         JNZ IDX360       ;SET, GO FOR ANOTHER REV
0170 213500  D  280         LXI H,CNTERR
0173 3E01      281         MVI M,1          ;SET COUNT ERROR SPECULATIVELY
0175 3A2800  D  282         LDA DTCTR
0178 FE10      283         CPI 16           ;CHECK COUNT
017A C27E01  C  284         JNZ IDX721       ;NOT 16, LEAVE ERROR FLAG SET
017D 35        285         DCR M            ;CLEAR FLAG
017E 2B        286 IDX721: DCX H
017F 3601      287         MVI M,1          ;SET READY FLAG
0181 113C00  D  288         LXI D,DTBUF
0184 216C00  D  289         LXI H,DTXBUF
0187 0E28      290         MVI C,40
0189 7E        291 IDX722: MOV A,M          ;MOVE DATA TO REAL BUFFER
```

```
LOC   OBJ        SEQ       SOURCE STATEMENT 018A  12         392           STAX D
018B  23         393           INX H
018C  13         394           INX D
018D  0D         395           DCR C
018E  C28901  C  396           JNZ IDX722
0191  AF         397           XRA A
0192  328800  D  398           STA IDXFLG    ;RESET INDEX FLAG
0195  328700  D  399           STA DETENA    ;DISABLE DETECTOR
0198  C39B01  C  400           JMP IDXRET
                 401       ;
                 402       ;RETURN FROM INTERRUPT...
                 403       ;
                 404       IDX180:
019B  213800  D  405       IDXRET: LXI H,IDXFLG
019E  34         406           INR M         ;INCREMENT FLAG
                 407       IDXIGN:
019F  E1         408       IDXRT2: POP H
01A0  D1         409           POP D
01A1  C1         410           POP B
01A2  F1         411           POP PSW
01A3  FB         412           EI
01A4  C9         413           RET
                 414       $ EJECT
                 415       ;   DETECTOR INTERRUPT DRIVER...
                 416       ;   CHECK FLAG BYTE FOR EACH DETECTOR AND CALL APPROPRIATE ROUTINE...
                 417       ;
                 418       DETINT: ;PUSH PSW   ;SAVE REGGIES...
                 419           ;PUSH B
                 420           ;PUSH D
                 421           ;PUSH H
01A5  3A3700  D  422           LDA DETENA    ;CHECK DISABLE FLAG
01A8  0F         423           RRC
01A9  D2C401  C  424           JNC DTIRT0    ;DISABLED...
01AC  DB24       425           IN FLAGS      ;GET FLAG BYTE
01AE  0F         426           RRC           ;DETECTOR A FLAG TO CARRY
01AF  DCCF01  C  427           CC DTAINT     ;SET, GO PROCESS IT
01B2  0F         428           RRC           ;DET B FLAG TO CARRY
01B3  DCE901  C  429           CC DTBINT
01B6  0F         430           RRC           ;DET C FLAG TO CARRY
01B7  DCF101  C  431           CC DTCINT
01BA  0F         432           RRC           ;DET D TO CARRY
01BB  DCFA01  C  433           CC DTDINT
01BE  E1         434       DTXRET: POP H
01BF  D1         435           POP D
01C0  C1         436           POP B
01C1  F1         437           POP PSW
01C2  FB         438           EI
01C3  C9         439           RET
01C4  DB20       440       DTIRT0: IN DTACTR
01C6  DB21       441           IN DTBCTR
01C8  DB22       442           IN DTCCTR
01CA  DB23       443           IN DTDCTR
01CC  C3BE01  C  444           JMP DTXRET
                 445       $ EJECT
                 446       ;   DETECTOR A INTERRUPT ROUTINE...GET FINE COUNT, COURSE COUNT, AND
                 447       ;   TOTAL FINE COUNT AND STORE IN BUFFER...
                 448       ;
                 449       ;
01CF  010000     450       DTAINT: LXI B,0   ;OUR DATA OFFSET
01D2  F5         451           PUSH PSW      ;PRESERVE AC
01D3  DB20       452           IN DTACTR     ;GET DATA
```

```
LOC  OBJ         SEQ      SOURCE STATEMENT

452 ;
                 453 ;
                 454 ; ENTER HERE WITH SC = FINE COUNT, B.C = DATA OFFSET
                 455 ;
01D5 2A2900   D  456 DTXINT: LHLD DTPTR
01D8 09          457        DAD B
01D9 77          458        MOV M,A         ;STORE FINE COUNT IN BUFFER
01DA 23          459        INX H
01DB DEE5        460        IN FCOUNT       ;TOTAL COUNT
01DD 77          461        MOV M,A         ;INTO BUFFER
01DE 23          462        INX H
01DF DE95        463        IN MRKCTR       ;MARK COUNT
01E1 77          464        MOV M,A
01E2 213900   D  465        LXI H,DTCTR
01E5 34          466        INR M           ;COUNT IT
01E6 F1          467        POP PSW
01E7 C9          468        RET             ;RETURN
                 469 ;
                 470 ;DETECTOR B INTERRUPT...
                 471 ;
01E8 010C00      472 DTBINT: LXI B,12
01EB F5          473        PUSH PSW
01EC DB01        474        IN DTBCTR
01EE C2D501   C  475        JMP DTXINT
                 476 ;
01F1 011800      477 DTCINT: LXI B,24
01F4 F5          478        PUSH PSW
01F5 DB02        479        IN DTCCTR
01F7 C2D501   C  480        JMP DTXINT
                 481
01FA 012400      482 DTDINT: LXI B,36
01FD F5          483        PUSH PSW
01FE DB03        484        IN DTDCTR
0200 C2D501   C  485        JMP DTXINT
                 486 $ EJECT
                 487 ; 8-BIT DIVIDE ROUTINE....DIVIDE B,C BY E AND RETURN QUO IN H,L
                 488 ;
0203 AF          489 DIV8:  XRA A
0204 93          490        SUB E           ;COMPLIMENT THE DIVISOR
0205 57          491        MOV D,A         ;TO REGISTER D OF D,E PAIR
0206 1E00        492        MVI E,0
0208 EB          493        XCHG            ;TO H,L ... WHICH IT WILL SHARE WITH QUO.
0209 110000      494        LXI D,0         ;CLEAR D,E
020C D5          495        PUSH D          ;CLEAR QUO
020D 1E09        496        MVI E,9         ;COUNTER FOR 8 BITS (+1)
                 497 ;
                 498 ;LOOP FOR NEXT BIT....ADD (MINUS) DIVISOR TO DIVIDEND, KEEP IT IF PLUS.
                 499 ;
020F E5          500 DIV8LP: PUSH H         ;SAVE DIVISOR
0210 09          501        DAD B           ;SUBTRACT
0211 D21602   C  502        JNC DIV82       ;MINUS...
0214 44          503        MOV B,H         ;UPDATE DIV'ND
0215 4D          504        MOV C,L
0216 E1          505 DIV82: POP H
0217 E3          506        XTHL            ;GET QUO
0218 7D          507        MOV A,L         ;SHIFT CARRY BIT IN
0219 17          508        RAL
021A 6F          509        MOV L,A
021B 7C          510        MOV A,H
021C 17          511        RAL
021D 67          512        MOV H,A
                 513 ;
```

```
LOC  OBJ        SEQ      SOURCE STATEMENT

514  ;NOW SHIFT DIVIER DOWN...
                515  ;
021E E3          516        XTHL
021F 37          517        STC
0220 7C          518        MOV A,H
0221 1F          519        RAR
0222 67          520        MOV H,A
0223 7D          521        MOV A,L
0224 1F          522        RAR
0225 6F          523        MOV L,A
0226 1D          524        DCR E           ;DECREMENT BIT COUNT
0227 C20F02  C   525        JNZ DIV8LP
022A E1          526        POP H
022B C9          527        RET
                528  $EJECT
                529        END
```

PUBLIC SYMBOLS

EXTERNAL SYMBOLS

USER SYMBOLS
| BIT0   | A 0001 | BIT1   | A 0002 | BIT2   | A 0004 | BIT3   | A 0008 | BIT4   | A 0010 | BIT5   | A 0020 | BIT6   | A 0040 |
|--------|--------|--------|--------|--------|--------|--------|--------|--------|--------|--------|--------|--------|--------|
| BIT7   | A 0080 | CHOUT  | C 0095 | CHOUT1 | C 0097 | CLRLP  | C 0009 | CLRST  | C 0060 | CNTERR | D 0035 | CRLF   | C 009F |
| DETACQ | C 0090 | DETA04 | C 00B6 | DETCHK | C 00EF | DETENA | D 0037 | DETINT | C 01A5 | DETRDY | C 0084 | DETHT  | C 00CC |
| DETXFR | C 00CB | DIGOUT | C 0079 | DIV8   | C 0203 | DIV82  | C 0216 | DIV8LP | C 020F | DNOLP  | C 0057 | DNOLP2 | C 005E |
| DNOUT  | C 0051 | DNOUT2 | C 0073 | DTACTR | A 0090 | DTAINT | C 01CF | DTBCTR | A 0081 | DTBINT | C 01E2 | DTBUF  | D 0020 |
| DTCCTR | A 0082 | DTCINT | C 01F1 | DTCTR  | D 0038 | DTDCTR | A 0083 | DTDINT | C 01FA | DTIRT0 | C 01C4 | DTPTR  | D 0029 |
| DTREG  | D 009C | DTXBUF | D 006C | DTXINT | C 0105 | DTXRET | C 01EE | ERRST  | C 008C | FCOUNT | A 0085 | FCTTBL | C 0082 |
| FLAGS  | A 0084 | IDX180 | C 0195 | IDX270 | C 0133 | IDX360 | C 013A | IDX450 | C 0154 | IDXIGN | C 019F | IDX630 | C 0160 |
| IDX720 | C 0169 | IDX721 | C 017E | IDX722 | C 0189 | IDX90  | C 012A | IDXFLG | D 0028 | IDXINT | C 0100 |        |        |
| IDXRET | C 0198 | IDXRT2 | C 019F | IDXRT3 | C 0163 | IDXTEL | C 011A | LOOP   | C 0018 | LOOP1  | C 002B | LOOP2  | C 0031 |
| MRKCTR | A 0086 | START  | C 0000 | STCK   | D 0032 | STOUT  | C 008B | THREG  | A 0080 | XFRFLG | D 0036 | XFRLP  | C 00D0 |

ASSEMBLY COMPLETE, NO ERRORS

```
001  *LBLA  21 11       021   -     -45        041  GTOb  22 15 12
002  CLX       -51      022  PRTX   -14        042  STOb  35 08
003  ST08   35 08       023  RCLC  36 13       043  P#S   16-51
004  ST09   35 09       024  RCLD  36 14       044  CLRG  16-53
005  ?         07       025   +    -55         045  P#S   16-51
006  STOI   35 46       026  RCLA  36 11       046  WDTA  16-61
007  *LBLa  21 16 11    027   -    -45         047  STOA  22 11
008  R/S       51       028  RCLB  36 12       048  *LBLb 21 16 12
009  STOD   35 14       029   -    -45         049  STOI  35 46
010  R↓       -31       030  ST+8 35-55 08     050  CLX   16 25 40
011  STOC   35 13       031  STOi  35 45       051  STOa  22 16 11
012  R↓       -31       032  RCLA  36 11       052  *LBLB 21 12
013  STOB   35 12       033  RCLB  36 12       053  CF3   16 22 03
014  R↓       -31       034   +    -55         054  GSBC  23 13
015  STOA   35 11       035  RCLC  36 13       055  RCL8  36 08
016  RCLD   36 14       036   +    -55         056  P#S   16-51
017   -       -55       037  RCLD  36 14       057  ST04  35 04
018  RCLC   36 13       038   +    -55         058  P#S   16-51
019   -       -45       039  ST+9 35-55 09     059  RCL9  36 09
020  RCLB   36 12       040  DSZI  16 25 46    060   .    -62
```

| | | | | | | | | | |
|---|---|---|---|---|---|---|---|---|---|
| 061 | 6 | 06 | 116 | RCLD | 36 14 | 170 | ST05 | 35 05 |
| 062 | 0 | 00 | 117 | 2 | 02 | 171 | ST06 | 35 06 |
| 063 | 0 | 00 | 118 | x | -35 | 172 | ST07 | 35 07 |
| 064 | 3 | 03 | 119 | COS | 42 | 173 | ST09 | 35 09 |
| 065 | 4 | 04 | 120 | x | -35 | 174 | RCL1 | 36 01 |
| 066 | 3 | 03 | 121 | - | -45 | 175 | RCL0 | 36 00 |
| 067 | 3 | 03 | 122 | √X | 54 | 176 | RCL4 | 36 04 |
| 068 | 2 | 02 | 123 | RCLA | 36 11 | 177 | x | -35 |
| 069 | 3 | 03 | 124 | RCLC | 36 13 | 178 | ÷ | -55 |
| 070 | P⇄S | 16-51 | 125 | - | -45 | 179 | ST04 | 35 04 |
| 071 | ST02 | 35 02 | 126 | ENT↑ | -21 | 180 | RCLA | 36 11 |
| 072 | x | -35 | 127 | ABS | 16 31 | 181 | RCL0 | 36 00 |
| 073 | CHS | -22 | 128 | ÷ | -24 | 182 | x | -35 |
| 074 | ST03 | 35 03 | 129 | x | -35 | 183 | RCL1 | 36 01 |
| 075 | P⇄S | 16-51 | 130 | ST+1 | 35-55 01 | 184 | + | -55 |
| 076 | GSBC | 23 13 | 131 | RCL0 | 36 00 | 185 | ENT↑ | -21 |
| 077 | RCL9 | 36 09 | 132 | ST÷1 | 35-24 01 | 186 | ENT↑ | -21 |
| 078 | P⇄S | 16-51 | 133 | RCLA | 36 11 | 187 | RCL4 | 36 04 |
| 079 | RCL2 | 36 02 | 134 | RCLC | 36 13 | 188 | - | -45 |
| 080 | x | -35 | 135 | RCL1 | 36 01 | 189 | ENT↑ | -21 |
| 081 | RCL3 | 36 03 | 136 | x | -35 | 190 | ABS | 16 31 |
| 082 | + | -55 | 137 | - | -45 | 191 | ÷ | -24 |
| 083 | ST01 | 35 01 | 138 | RCL1 | 36 01 | 192 | x | -35 |
| 084 | P⇄S | 16-51 | 139 | 1 | 01 | 193 | RCL5 | 36 12 |
| 085 | RCL6 | 36 06 | 140 | - | -45 | 194 | SIN | 41 |
| 086 | P⇄S | 16-51 | 141 | ÷ | -24 | 195 | x | -35 |
| 087 | ST00 | 35 00 | 142 | ST01 | 35 01 | 196 | RCLE | 36 15 |
| 088 | P⇄S | 16-51 | 143 | 5 | 05 | 197 | ÷ | -24 |
| 089 | GSBC | 23 13 | 144 | . | -62 | 198 | SIN⁻¹ | 16 41 |
| 090 | RCL9 | 36 09 | 145 | 9 | 09 | 199 | 9 | 09 |
| 091 | P⇄S | 16-51 | 146 | 0 | 00 | 200 | 0 | 00 |
| 092 | RCL2 | 36 02 | 147 | ST0E | 35 15 | 201 | . | -62 |
| 093 | x | -35 | 148 | RCLA | 36 11 | 202 | 0 | 00 |
| 094 | RCL3 | 36 03 | 149 | RCL1 | 36 01 | 203 | - | -45 |
| 095 | ÷ | -55 | 150 | - | -55 | 204 | ST08 | 35 08 |
| 096 | ST0D | 35 14 | 151 | RCLB | 36 12 | 205 | 4 | 04 |
| 097 | P⇄S | 16-51 | 152 | SIN | 41 | 206 | STx2 | 35-35 02 |
| 098 | RCL8 | 36 08 | 153 | x | -35 | 207 | ST÷1 | 35-24 01 |
| 099 | ST0C | 35 13 | 154 | ENT↑ | -21 | 208 | ST÷4 | 35-24 04 |
| 100 | P⇄S | 16-51 | 155 | x | -35 | 209 | P⇄S | 16-51 |
| 101 | RCL0 | 36 00 | 156 | RCLC | 36 13 | 210 | CLRG | 16-53 |
| 102 | ST0A | 35 11 | 157 | RCL1 | 36 01 | 211 | P⇄S | 16-51 |
| 103 | RCL1 | 36 01 | 158 | + | -55 | 212 | WDTA | 16-61 |
| 104 | ST0B | 35 12 | 159 | RCLD | 36 14 | 213 | PREG | 16-13 |
| 105 | RCL1 | 36 01 | 160 | SIN | 41 | 214 | RTN | 24 |
| 106 | - | -45 | 161 | x | -35 | 215 | *LBLC | 21 13 |
| 107 | COS | 42 | 162 | ENT↑ | -21 | 216 | 9 | 09 |
| 108 | ST01 | 35 01 | 163 | x | -35 | 217 | ST0I | 35 46 |
| 109 | ENT↑ | -21 | 164 | + | -55 | 218 | F3? | 16 23 03 |
| 110 | x | -35 | 165 | √X | 54 | 219 | RTN | 24 |
| 111 | RCLB | 36 12 | 166 | ÷ | -24 | 220 | MRG | 16-62 |
| 112 | 2 | 02 | 167 | ST00 | 35 00 | 221 | PSE | 16 51 |
| 113 | x | -35 | 168 | STx1 | 35-35 01 | 222 | GT0C | 22 13 |
| 114 | COS | 42 | 169 | CLX | -51 | 223 | R/S | 51 |
| 115 | ST0B | 35 00 | | | | | | |

| | | | | | | | | | |
|---|---|---|---|---|---|---|---|---|---|
| 001 | *LBLA | 21 11 | 006 | RTN | 24 | 011 | P⇄S | 16-51 |
| 002 | 9 | 09 | 007 | MRG | 16-62 | 012 | RCL0 | 36 00 |
| 003 | ST0I | 35 46 | 008 | PSE | 16 51 | 013 | x | -35 |
| 004 | 0 | 00 | 009 | ST0A | 22 11 | 014 | RCL1 | 36 01 |
| 005 | F3? | 16 23 03 | 010 | *LBLB | 21 12 | 015 | ÷ | -55 |

| | | | | | | | | | |
|---|---|---|---|---|---|---|---|---|---|
| 016 | X≷Y | -41 | 073 | TAN⁻¹ | 16 43 | 129 | ST-8 | 35-45 08 |
| 017 | RCL2 | 36 02 | 074 | ENT↑ | -21 | 130 | X≷Y | -41 |
| 018 | × | -35 | 075 | ENT↑ | -21 | 131 | ST+8 | 35-55 08 |
| 019 | RCL3 | 36 03 | 076 | ABS | 16 31 | 132 | RCL8 | 36 08 |
| 020 | + | -55 | 077 | ÷ | -24 | 133 | STOE | 35 15 |
| 021 | X≷Y | -41 | 078 | 1 | 01 | 134 | 7 | 07 |
| 022 | →R | 44 | 079 | + | -55 | 135 | STOI | 35 46 |
| 023 | RCL4 | 36 04 | 080 | 9 | 09 | 136 | GSBA | 23 11 |
| 024 | - | -45 | 081 | 0 | 00 | 137 | CLX | -51 |
| 025 | X≷Y | -41 | 082 | × | -35 | 138 | ST08 | 35 08 |
| 026 | RCL5 | 36 05 | 083 | - | -45 | 139 | RCL6 | 36 06 |
| 027 | - | -45 | 084 | STOA | 35 11 | 140 | RCL7 | 36 07 |
| 028 | X≷Y | -41 | 085 | P≷S | 16-51 | 141 | GSBB | 23 12 |
| 029 | P≷S | 16-51 | 086 | CHS | -22 | 142 | ST-8 | 35-45 08 |
| 030 | RTN | 24 | 087 | RCL8 | 36 08 | 143 | X≷Y | -41 |
| 031 | *LBLC | 21 13 | 088 | + | -55 | 144 | ST-8 | 35-45 08 |
| 032 | CF3 | 16 22 03 | 089 | ST09 | 35 09 | 145 | RCL4 | 36 04 |
| 033 | P≷S | 16-51 | 090 | RCL3 | 36 03 | 146 | RCL5 | 36 05 |
| 034 | GSBA | 23 11 | 091 | RCLA | 36 11 | 147 | GSBB | 23 12 |
| 035 | CLX | -51 | 092 | - | -45 | 148 | ST+8 | 35-55 08 |
| 036 | ST08 | 35 08 | 093 | ST03 | 35 03 | 149 | X≷Y | -41 |
| 037 | ST09 | 35 09 | 094 | RCL5 | 36 05 | 150 | ST-8 | 35-45 08 |
| 038 | RCL6 | 36 06 | 095 | RCL4 | 36 04 | 151 | RCL2 | 36 02 |
| 039 | RCL7 | 36 07 | 096 | →P | 34 | 152 | RCL3 | 36 03 |
| 040 | GSBB | 23 12 | 097 | X≷Y | -41 | 153 | GSBB | 23 12 |
| 041 | ST+8 | 35-55 08 | 098 | RCLA | 36 11 | 154 | ST+8 | 35-55 08 |
| 042 | ST-9 | 35-45 09 | 099 | - | -45 | 155 | X≷Y | -41 |
| 043 | X≷Y | -41 | 100 | X≷Y | -41 | 156 | ST+8 | 35-55 08 |
| 044 | ST-8 | 35-45 08 | 101 | →R | 44 | 157 | RCL0 | 36 00 |
| 045 | ST-9 | 35-45 09 | 102 | ST04 | 35 04 | 158 | RCL1 | 36 01 |
| 046 | RCL4 | 36 04 | 103 | R↓ | -31 | 159 | GSBB | 23 12 |
| 047 | RCL5 | 36 05 | 104 | ST05 | 35 05 | 160 | ST-8 | 35-45 08 |
| 048 | GSBB | 23 12 | 105 | P≷S | 16-51 | 161 | X≷Y | -41 |
| 049 | ST+8 | 35-55 08 | 106 | CLX | -51 | 162 | ST+8 | 35-55 08 |
| 050 | ST+9 | 35-55 09 | 107 | ST08 | 35 08 | 163 | RCL8 | 36 08 |
| 051 | X≷Y | -41 | 108 | RCL6 | 36 06 | 164 | STOC | 35 13 |
| 052 | ST+8 | 35-55 08 | 109 | RCL7 | 36 07 | 165 | RCLE | 36 15 |
| 053 | ST-9 | 35-45 09 | 110 | GSBB | 23 12 | 166 | - | -45 |
| 054 | RCL2 | 36 02 | 111 | ST-8 | 35-45 08 | 167 | CHS | -22 |
| 055 | RCL3 | 36 03 | 112 | X≷Y | -41 | 168 | 9 | 09 |
| 056 | GSBB | 23 12 | 113 | ST-8 | 35-45 08 | 169 | . | -62 |
| 057 | ST-8 | 35-45 08 | 114 | RCL4 | 36 04 | 170 | 8 | 08 |
| 058 | ST+9 | 35-55 09 | 115 | RCL5 | 36 05 | 171 | 0 | 00 |
| 059 | X≷Y | -41 | 116 | GSBB | 23 12 | 172 | ÷ | -24 |
| 060 | ST+8 | 35-55 08 | 117 | ST+8 | 35-55 08 | 173 | 1/X | 52 |
| 061 | ST+9 | 35-55 09 | 118 | X≷Y | -41 | 174 | P≷S | 16-51 |
| 062 | RCL0 | 36 00 | 119 | ST-8 | 35-45 08 | 175 | ST06 | 35 06 |
| 063 | RCL1 | 36 01 | 120 | RCL2 | 36 02 | 176 | RCLC | 36 13 |
| 064 | GSBB | 23 12 | 121 | RCL3 | 36 03 | 177 | × | -35 |
| 065 | ST-8 | 35-45 08 | 122 | GSBB | 23 12 | 178 | ST07 | 35 07 |
| 066 | ST-9 | 35-45 09 | 123 | ST+8 | 35-55 08 | 179 | P≷S | 16-51 |
| 067 | X≷Y | -41 | 124 | X≷Y | -41 | 180 | CLRG | 16-53 |
| 068 | ST-8 | 35-45 08 | 125 | ST+8 | 35-55 08 | 181 | P≷S | 16-51 |
| 069 | ST-9 | 35-55 09 | 126 | RCL0 | 36 00 | 182 | WDTA | 16-61 |
| 070 | RCL8 | 36 08 | 127 | RCL1 | 36 01 | 183 | PRGG | 16-13 |
| 071 | RCL9 | 36 09 | 128 | GSBB | 23 12 | 184 | RTN | 24 |
| 072 | ÷ | -24 | | | | 185 | R/S | 51 |

| | | | | | | | | | |
|---|---|---|---|---|---|---|---|---|---|
| 001 | *LBLA | 21 11 | 066 | ÷ | -24 | 130 | X>0? | 16-44 |
| 002 | RCL0 | 36 00 | 067 | STOE | 35 15 | 131 | GTO1 | 22 01 |
| 003 | CHS | -22 | 068 | RCL2 | 36 02 | 132 | CHS | -22 |
| 004 | 6 | 06 | 069 | 3 | 03 | 133 | STO1 | 35 01 |
| 005 | 5 | 05 | 070 | 6 | 06 | 134 | 1 | 01 |
| 006 | 5 | 05 | 071 | 0 | 00 | 135 | STO2 | 35 02 |
| 007 | 3 | 03 | 072 | ÷ | -24 | 136 | *LBL1 | 21 01 |
| 008 | 6 | 06 | 073 | STO2 | 35 02 | 137 | RCL1 | 36 01 |
| 009 | × | -35 | 074 | RCL3 | 36 03 | 138 | X=0? | 16-43 |
| 010 | STO0 | 35 00 | 075 | 3 | 03 | 139 | GTO4 | 22 04 |
| 011 | RCL1 | 36 01 | 076 | 6 | 06 | 140 | 1 | 01 |
| 012 | CHS | -22 | 077 | 0 | 00 | 141 | X≤Y? | 16-35 |
| 013 | STO1 | 35 01 | 078 | ÷ | -24 | 142 | GTO2 | 22 02 |
| 014 | RCL2 | 36 02 | 079 | STO3 | 35 03 | 143 | 2 | 02 |
| 015 | 6 | 06 | 080 | RCL8 | 36 08 | 144 | ÷ | -24 |
| 016 | 5 | 05 | 081 | 3 | 03 | 145 | X>Y? | 16-34 |
| 017 | 5 | 05 | 082 | 6 | 06 | 146 | GTO3 | 22 03 |
| 018 | 3 | 03 | 083 | 0 | 00 | 147 | RCL1 | 36 01 |
| 019 | 6 | 06 | 084 | ÷ | -24 | 148 | *LBL4 | 21 04 |
| 020 | × | -35 | 085 | STO8 | 35 08 | 149 | 2 | 02 |
| 021 | STO2 | 35 02 | 086 | FIX | -11 | 150 | 5 | 05 |
| 022 | RCL4 | 36 04 | 087 | DSP6 | -63 06 | 151 | 6 | 06 |
| 023 | CHS | -22 | 088 | PREG | 16-13 | 152 | × | -35 |
| 024 | STO4 | 35 04 | 089 | RCL0 | 36 00 | 153 | ENT↑ | -21 |
| 025 | RCL5 | 36 05 | 090 | GSBB | 23 12 | 154 | INT | 16 34 |
| 026 | CHS | -22 | 091 | RCL1 | 36 01 | 155 | STO4 | 35 04 |
| 027 | STO5 | 35 05 | 092 | GSBB | 23 12 | 156 | − | -45 |
| 028 | RCL6 | 36 06 | 093 | RCL2 | 36 02 | 157 | 2 | 02 |
| 029 | CHS | -22 | 094 | GSBB | 23 12 | 158 | 5 | 05 |
| 030 | STO6 | 35 06 | 095 | RCL3 | 36 03 | 159 | 6 | 06 |
| 031 | RCL8 | 36 08 | 096 | GSBB | 23 12 | 160 | × | -35 |
| 032 | SIN | 41 | 097 | RCL4 | 36 04 | 161 | ENT↑ | -21 |
| 033 | STO9 | 35 09 | 098 | GSBB | 23 12 | 162 | INT | 16 34 |
| 034 | RCL8 | 36 08 | 099 | RCL5 | 36 05 | 163 | STO3 | 35 03 |
| 035 | COS | 42 | 100 | GSBB | 23 12 | 164 | FIX | -11 |
| 036 | STOA | 35 11 | 101 | RCL6 | 36 06 | 165 | DSP0 | -63 00 |
| 037 | RCL5 | 36 05 | 102 | GSBB | 23 12 | 166 | RCL5 | 36 05 |
| 038 | 4 | 04 | 103 | RCL7 | 36 07 | 167 | X=0? | 16-43 |
| 039 | × | -35 | 104 | GSBB | 23 12 | 168 | GTO5 | 22 05 |
| 040 | STOB | 35 12 | 105 | RCL8 | 36 08 | 169 | X>0? | 16-44 |
| 041 | PI | 16-24 | 106 | GSBB | 23 12 | 170 | GTO5 | 22 05 |
| 042 | RCL2 | 36 02 | 107 | RCL9 | 36 09 | 171 | 2 | 02 |
| 043 | × | -35 | 108 | GSBB | 23 12 | 172 | 5 | 05 |
| 044 | RCLB | 36 12 | 109 | RCLA | 36 11 | 173 | 6 | 06 |
| 045 | × | -35 | 110 | GSBB | 23 12 | 174 | + | -55 |
| 046 | 7 | 07 | 111 | RCLB | 36 12 | 175 | *LBL5 | 21 05 |
| 047 | 2 | 02 | 112 | GSBB | 23 12 | 176 | RCL2 | 36 02 |
| 048 | 0 | 00 | 113 | RCLC | 36 13 | 177 | RCL3 | 36 03 |
| 049 | ÷ | -24 | 114 | GSBB | 23 12 | 178 | RCL4 | 36 04 |
| 050 | RCL0 | 36 00 | 115 | RCLD | 36 14 | 179 | R↑ | 16-31 |
| 051 | STOD | 35 14 | 116 | GSBB | 23 12 | 180 | PRST | 16-14 |
| 052 | PI | 16-24 | 117 | RCLE | 36 15 | 181 | P≠S | 16-51 |
| 053 | 4 | 04 | 118 | GSBB | 23 12 | 182 | RTN | 24 |
| 054 | × | -35 | 119 | R/S | 51 | 183 | GTOB | 22 12 |
| 055 | RCL3 | 36 03 | 120 | *LBLB | 21 12 | 184 | *LBL2 | 21 02 |
| 056 | 9 | 09 | 121 | P≠S | 16-51 | 185 | RCL1 | 36 01 |
| 057 | 0 | 00 | 122 | FIX | -11 | 186 | 2 | 02 |
| 058 | − | -45 | 123 | DSP6 | -63 06 | 187 | ÷ | -24 |
| 059 | × | -35 | 124 | PRTX | -14 | 188 | STO1 | 35 01 |
| 060 | RCLB | 36 12 | 125 | STO1 | 35 01 | 189 | RCL5 | 36 05 |
| 061 | × | -35 | 126 | CLX | -51 | 190 | 1 | 01 |
| 062 | 7 | 07 | 127 | STO2 | 35 02 | 191 | + | -55 |
| 063 | 2 | 02 | 128 | STO5 | 35 05 | 192 | STO5 | 35 05 |
| 064 | 0 | 00 | 129 | RCL1 | 36 01 | 193 | GTO1 | 22 01 |

```
194  *LBL3    21 03        198  ST01     35 01        202  ST05     35 05
195  RCL1     36 01        199  RCL5     36 05        203  GT01     22 01
196  2           02        200  1           01        204  R/S         51
197  x          -35        201  -          -45

001  *LBLA    21 11        053  GSBB     23 12        105  INT      16 34
002  2           02        054  DSP6    -63 06        106  ST04     35 04
003  0           00        055  GTOA     22 11        107  -          -45
004  .          -62        056  *LBLa 21 16 11        108  2           02
005  0           00        057  2           02        109  5           05
006  4           04        058  x          -35        110  6           06
007  ST04     35 04        059  X≷Y       -41        111  x          -35
008  R/S         51        060  ÷R          44        112  ENT↑      -21
009  GSBa  23 16 11        061  RTN         24        113  INT      16 34
010  ST01     35 01        062  *LBLb 21 16 12        114  ST03     35 03
011  R↓         -31        063  R↑       16-31        115  FIX        -11
012  ST00     35 00        064  →P          34        116  DSP0    -63 00
013  GSBb  23 16 12        065  X≷Y       -41        117  RCL5     36 05
014  ST08     35 08        066  R↓         -31        118  X=0?    16-43
015  R/S         51        067  2           02        119  GT05     22 05
016  GSBa  23 16 11        068  ÷          -24        120  X>0?    16-44
017  ST-1  35-45 01        069  ÷          -55        121  GT05     22 05
018  R↓         -31        070  RTN         24        122  2           02
019  ST-0  35-45 00        071  *LBLB    21 12        123  5           05
020  GSBb  23 16 12        072  P≷S      16-51        124  6           06
021  ST09     35 09        073  FIX        -11        125  +          -55
022  RCL4     36 04        074  DSP6    -63 06        126  *LBL5    21 05
023  ST÷0  35-24 00        075  PRTX       -14        127  RCL2     36 02
024  ST÷1  35-24 01        076  ST01     35 01        128  RCL3     36 03
025  R/S         51        077  CLX        -51        129  RCL4     36 04
026  x          -35        078  ST02     35 02        130  R↑       16-31
027  RCL8     36 08        079  ST05     35 05        131  PRST     16-14
028  RCL9     36 09        080  RCL1     36 01        132  P≷S      16-51
029  -          -45        081  X>0?    16-44        133  RTN         24
030  ÷          -24        082  GT01     22 01        134  GTOB     22 12
031  ST02     35 02        083  CHS        -22        135  *LBL2    21 02
032  RCL8     36 08        084  ST01     35 01        136  RCL1     36 01
033  RCL9     36 09        085  1           01        137  2           02
034  +          -55        086  ST02     35 02        138  ÷          -24
035  .          -62        087  *LBL1    21 01        139  ST01     35 01
036  2           02        088  RCL1     36 01        140  RCL5     36 05
037  1           01        089  X=0?    16-43        141  1           01
038  +          -55        090  GT04     22 04        142  +          -55
039  5           05        091  1           01        143  ST05     35 05
040  x          -35        092  X≤Y?     16-35        144  GT01     22 01
041  EEX        -23        093  GT02     22 02        145  *LBL3    21 03
042  CHS        -22        094  2           02        146  RCL1     36 01
043  3           03        095  ÷          -24        147  2           02
044  x          -35        096  X>Y?     16-34        148  x          -35
045  ST03     35 03        097  GT03     22 03        149  ST01     35 01
046  RCL0     36 00        098  RCL1     36 01        150  RCL5     36 05
047  GSBB     23 12        099  *LBL4    21 04        151  1           01
048  RCL1     36 01        100  2           02        152  -          -45
049  GSBB     23 12        101  5           05        153  ST05     35 05
050  RCL2     36 02        102  6           06        154  GT01     22 01
051  GSBB     23 12        103  x          -35        155  R/S         51
052  RCL3     36 03        104  ENT↑      -21
```

```
001  *LBLA    21 11        019  P≠S     16-51         037  GTOb   22 16 12
002  CF3   16 22 03        020  RCLA    36 11         038  ST=0   35-24 00
003  CLRG     16-53        021    1        01         039  P≠S      16-51
004  P≠S      16-51        022    +       -55         040  CLRG     16-53
005  CLRG     16-53        023  STOA    35 11         041  P≠S      16-51
006  CLX        -51        024    4        04         042  WDTA     16-61
007  STOA    35 11         025  X=Y?    16-33         043  FREG     16-13
008  GSBC    23 13         026  GTOE    22 12         044  RTN         24
009  *LBLa   21 16 11      027  GSBC    23 13         045  *LBLC    21 13
010  RCLI    36 45         028  GTOa    22 16 11      046    9         09
011  P≠S      16-51        029  *LBLB   21 12         047  STOI     35 46
012  ST+i   35-55 45       030    9        09         048  F3?    16 23 03
013  P≠S      16-51        031  STOI    35 46         049  RTN         24
014  DSZI   16 25 46       032  P≠S     16-51         050  MRG      16-62
015  GTOa   22 16 11       033  *LBLk   21 16 12      051  PSE      16 51
016  RCL0    36 00         034    4        04         052  GTOC     22 13
017  P≠S      16-51        035  ST=i    35-24 45      053  RTN         24
018  ST+0   35-55 00       036  DSZI   16 25 46       054   ÷ 3        51
```

I claim:

1. A process for assembling and calibrating an instrument which measures optical parameters of a suspect optical system placed within a sampling interval, the instrument having its own optical train of assembled optical elements including a light source, a detector, and means for measuring deflection of light between the light source and the detector caused by the suspect optical system, the instrument also having a dedicated computer for converting the measured deflections into a desired form of optical parameters of the suspect optical system, the dedicated computer having a CPU, the dedicated computer further making use of a plurality of constants stored in a memory unit, the assembly and calibration process comprising the steps of: permanently assembling the optical train to loose production tolerances; placing sequentially a sequence of optical test elements, each of which test elements has known deflection-causing properties, within the sampling interval; storing the deflections caused by the test elements in combination with the instrument; calculating the plurality of constants on the basis of the values of the stored deflections and the known deflection causing properties of the test elements; writing the calculated constants into the memory unit; and connecting the memory unit with the dedicated computer.

2. A process for calibrating an instrument which measures optical parameters of a suspect optical system placed within a sampling interval, the instrument having its own optical train of optical elements which have been assembled to loose production tolerances, the train including a light source, a detector, and means for generating raw data representative of deflection of light between the light source and the detector caused by the suspect optical system, the instrument also having a dedicated computer for converting the deflection data into a desired form of optical parameters of the suspect optical system, the dedicated computer having a CPU, the dedicated computer further making use of a plurality of constants stored in a memory unit, the calibration process comprising the steps of: placing sequentially within the sampling interval a sequence of optical test elements, each of which test elements has known deflection-causing properties; storing raw data representative of the deflections caused by the test elements in combination with the instrument; calculating the plurality of constants on the basis of the values of the stored deflections and the known deflection causing properties of the test elements; writing the calculated constants into the memory unit; and connecting the memory unit with the dedicated computer.

3. The invention of claim 1 or 2 also including the step of first connecting the instrument to an external computer, and wherein the calculating step is carried out by the external computer.

4. The invention of claim 1 or 2 wherein the calculating step is carried out by the dedicated computer.

5. A process for assembling and calibrating an instrument which measures optical parameters of a suspect optical system placed within a sampling interval, the instrument having its own optical train of assembled optical elements including a light source, a detector, and means for measuring deflection of light between the light source and the detector caused by the suspect optical system, the instrument also having a dedicated computer for converting the measured deflections into a desired form of optical parameters of the suspect optical system, the dedicated computer having a CPU, the dedicated computer further making use of a plurality of constants stored in a memory unit, the assembly and calibration process comprising the steps of: permanently assembling the optical train to loose production tolerances; connecting the instrument to an external computer; placing sequentially a sequence of optical test elements, each of which test elements has known deflection-causing properties, within the sampling interval; storing in the external computer the deflections caused by the test elements in combination with the instrument; calculating in the external computer the plurality of constants on the basis of the values of the stored deflections and the known deflection-causing properties of the test elements; writing the calculated constants into the memory unit; disconnecting the outside computer; activating the dedicated computer's CPU; and connecting the memory unit with the dedicated computer.

6. A process for calibrating an instrument which measures optical parameters of a subject optical system placed within a sampling interval, the instrument having its own optical train of optical elements which have been assembled to loose production tolerances, the train including a light source, a detector, and means for generating raw data representative of deflection of light between the light source and the detector caused by the subject optical system, the instrument also having a dedicated computer for converting the deflection data into a desired form of optical parameters of the suspect optical system, the dedicated computer having a CPU, the dedicated computer further making use of a plurality of constants stored in a memory unit, the calibration process comprising the steps of: connecting the instrument to an external computer; placing sequentially within the sampling interval a sequence of optical test elements, each of which test elements has known deflection-causing properties; storing in the external computer raw data representative of the deflections caused by the test elements in combination with the instrument; calculating in the external computer the plurality of constants on the basis of the values of the stored deflections and the known deflection-causing properties of the test elements; writing the calculated constants into the memory unit; disconnecting the outside computer; activating the dedicated computer's CPU; and connecting the memory unit with the dedicated computer.

7. The process of claim 5 or 6 wherein the step of connecting the instrument to an external computer occurs with the dedicated computer's CPU physically absent from the instrument 8. The process of claim 5 or 6 wherein the step of writing the constants into the memory unit occurs with the memory unit physically absent from the instrument.

9. The process of claim 5 or 6 also including the steps of generating raw data representative of the deflection that results when no test element is within the sampling interval, and storing in the external computer the deflection data that results when no test element is within the sampling interval.

10. The process of claim 9 wherein the step of placing sequentially a sequence of optical test elements within the sampling interval comprises the sub steps of: placing a prism test element in the sampling interval at a first orientation; placing the prism test element in the sampling interval at a second orientation having a known angular displacement from the first orientation; and placing a test element having known sphere power in the sampling interval.

11. The process of claim 10 wherein the step of calculating in the external computer the plurality of constants includes the following sub steps: calculating geometric scale factors and points of origin which permit the transformation of raw data into cartesian deflections on the basis of the deflections generated by the instrument when no element and when the prism element are in the sampling interval; computing a first set of cartesian deflections from the deflection data generated when the test element having sphere power is in the sampling interval; correcting the first set of geometric scale factors and points of origin to cause a zero-going test function to vanish, thereby generating a second set of geometric scale factors and points of origin; computing a second corrected set of cartesian deflections from the deflection data generated by the instrument when no test element and when the test element having sphere power is in the sampling interval; and using the second set of corrected deflection to compute an optical scale factor and points of origin.

12. Apparatus for calibrating an instrument which measures optical parameters of a suspect optical system placed within a sampling interval, the instrument having a light source, a detector, and means for generating raw data representative of deflections of the light from the light source to the detector caused by the suspect optical system, the instrument having its own optical train of elements assembled to loose production tolerances, the instrument also having a dedicated computer for converting the deflection data into a desired form of optical parameters of the suspect optical system, the dedicated computer making use of a plurality of constants stored in a memory, the calibration apparatus comprising: a test optical element that has known optical parameters; means for receiving the deflection data resulting when the test element is placed within the sampling interval; arithmetic means for calculating the plurality of constants on the basis of the deflection data; and means for writing the constants into the memory.

13. The calibration apparatus of claim 12 wherein the arithmetic means is separate from the dedicated computer.

14. The calibration apparatus of claim 12 wherein the means for writing the constants into the memory is separate from the dedicated computer.

15. The calibration apparatus of claim 14 in which the memory is a ROM and the means for writing the constants into the memory comprises a ROM mapper.

16. A process for calibrating an instrument which measures optical parameters of a suspect optical system placed within a sampling interval, the instrument having its own optical train of optical elements which has been assembled to loose production tolerances, the train including a light source, a detector, and means for generating raw data representative of the deflection of light between the light source and the detector caused by the suspect optical system, the instrument also having a dedicated computer for converting the deflection data into a desired form of optical parameters of the suspect optical system, the dedicated computer having a CPU, the dedicated computer further making use of a plurality of constants stored in a memory unit in order to perform the conversion from deflection data to optical parameters, the calibration process comprising the steps of:

causing the data generating means to generate a first set of data representative of the deflections that occur when no element is placed in the sampling interval;

placing a prism test element in the sampling interval at a first orientation;

causing the data generation means to generate a second set of raw data representative of the deflections caused by the prism in the sampling interval at the first orientation;

placing the prism in the sampling interval at a second orientation, the relationship between the first orientation and the second orientation being fixed and known;

causing the data generation means to generate a third set of data representative of the deflections caused by the prism at its second orientation in the sampling interval;

placing a test element having sphere power in the sampling interval;

causing the data generation means to generate a fourth set of data representative of deflections caused by the test element having sphere power in the sampling interval;

calculating a first set of geometric scale factors and points of origin on the basis of the first, second, and third sets of data, the geometric scale factors and points of origin making possible the conversion from the form of deflection data to the form of cartesian deflections;

calculating a first set of cartesian deflections caused by the test element having sphere power in the sampling interval on the basis of the first set of geometric scale factors and points of origin and the fourth set of data;

using the first set of cartesian deflections to correct the first set of geometric constants, thereby generating a second set of geometric scale factors and points of origin;

calculating a second set of cartesian deflections caused by having no test element in the sampling interval on the basis of the second set of geometrical scale factors and points of origin and the first set of data;

calculating a third set of cartesian deflections caused by the test element having sphere power in the sampling interval on the basis of the second set of geometric scale factors and points of origin and the fourth set of data;

calculating an optical scale factor and points of origin on the basis of the second and third sets of cartesian deflections;

writing the second set of geometrical scale factors and points of origin and the optical scale factor and points of origin into the memory unit;

connecting the memory unit with the dedicated computer.

17. The process of claim 16 wherein the data generating means includes a moving boundary locus, and wherein the deflection data are counter values at occulation times.

18. The process of claim 16 also comprising the step of first connecting the instrument to an external computer, and wherein the calculating steps are carried out by the external computer.

19. The process of claim 16 wherein the calculating steps are carried out by the dedicated computer.

* * * * *